US011077120B2

(12) United States Patent
Ganesh et al.

(10) Patent No.: US 11,077,120 B2
(45) Date of Patent: Aug. 3, 2021

(54) PROSTAGLANDIN RECEPTOR EP2 ANTAGONISTS, DERIVATIVES, COMPOSITIONS, AND USES RELATED THERETO

(71) Applicant: Emory University, Atlanta, GA (US)

(72) Inventors: Thota Ganesh, Alpharetta, GA (US); Jianxiong Jiang, Memphis, TN (US); Raymond Dingledine, Norcross, GA (US)

(73) Assignee: Emory University, Atlanta, GA (US)

( * ) Notice: Subject to any disclaimer, the term of this patent is extended or adjusted under 35 U.S.C. 154(b) by 52 days.

(21) Appl. No.: 16/686,046

(22) Filed: Nov. 15, 2019

(65) Prior Publication Data
US 2020/0085837 A1 Mar. 19, 2020

Related U.S. Application Data

(60) Division of application No. 16/037,374, filed on Jul. 17, 2018, now Pat. No. 10,568,889, which is a continuation of application No. 15/307,051, filed as application No. PCT/US2015/026364 on Apr. 17, 2015, now Pat. No. 10,052,332.

(60) Provisional application No. 61/985,608, filed on Apr. 29, 2014.

(51) Int. Cl.
| | |
|---|---|
| *A61K 31/551* | (2006.01) |
| *A61K 45/06* | (2006.01) |
| *A61K 31/4184* | (2006.01) |
| *A61K 31/4192* | (2006.01) |
| *A61K 31/454* | (2006.01) |
| *A61K 31/496* | (2006.01) |
| *A61K 31/506* | (2006.01) |
| *A61K 31/517* | (2006.01) |
| *A61K 31/5377* | (2006.01) |
| *A61K 31/55* | (2006.01) |

(52) U.S. Cl.
CPC ........ *A61K 31/551* (2013.01); *A61K 31/4184* (2013.01); *A61K 31/4192* (2013.01); *A61K 31/454* (2013.01); *A61K 31/496* (2013.01); *A61K 31/506* (2013.01); *A61K 31/517* (2013.01); *A61K 31/5377* (2013.01); *A61K 31/55* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,342,851 | A | 8/1994 | SanFilippo et al. |
| 9,518,044 | B2 | 12/2016 | Jiang et al. |
| 2005/0277773 | A1 | 12/2005 | Kataoka et al. |
| 2009/0163545 | A1 | 6/2009 | Goldfarb |
| 2017/0081314 | A1 | 3/2017 | Jiang et al. |

FOREIGN PATENT DOCUMENTS

| | | |
|---|---|---|
| CN | 01157668 | 4/2008 |
| EP | 2002838 | 12/2008 |
| EP | 2014287 | 1/2009 |
| EP | 2476667 | 7/2012 |
| JP | 2008115088 | 5/2008 |
| WO | 1999031064 | 6/1999 |
| WO | 2004035525 | 4/2004 |
| WO | 2008152097 | 12/2008 |
| WO | 2008152099 | 12/2008 |
| WO | 2009022104 | 2/2009 |
| WO | 2009147121 | 12/2009 |
| WO | 2010012396 | 2/2010 |
| WO | 2010012397 | 2/2010 |
| WO | 2010100606 | 9/2010 |
| WO | 2012080220 | 6/2012 |
| WO | 2012177618 | 12/2012 |

OTHER PUBLICATIONS

Battaglia et al. Indole amide derivatives: synthesis, structure—activity relationships and molecular modelling studies of a new series of histamine H1-receptor antagonists, Eur J Med Chem., vol. 34, Issue 2, Feb. 1999, pp. 93-105.
Fu et al. EP2 Receptor Signaling Regulates Microglia Death, Mol Pharmacol 88:161-170, Jul. 2015.
Ganesh et al. Development of second generation EP2 antagonists with high selectivity, Eur J Med Chem. Jul. 23, 2014; 82: 521-535.
Ganesh et al. Lead Optimization Studies of Cinnamic Amide EP2 Antagonists, J. Med. Chem., 2014,57 (10), pp. 4173-4184.
Ganesh, et al . . . , Peripherally restricted, highly potent, selective, aqueous-soluble EP2 antagonist with anti-inflammatory properties. Molecular pharmaceutics, 15(12), 2018, 5809-5817.
Jiang et al. Prostaglandin receptor EP2 in the crosshairs of anti-inflammation, anti-cancer, and neuroprotection, Trends in Pharmacological Sciences, 2013, vol. 34, No. 7,413-420.
Jiang et al. Small molecule antagonist reveals seizure-induced mediation of neuronal injury by prostaglandin E2 receptor subtype EP2. Proc Natl Acad Sci U S A. 2012;109(8):3149-54.
Jiang et al. Therapeutic window for cyclooxygenase-2 related anti-inflammatory therapy after status epilepticus, Neurobiology of Disease 76 (2015) 126-136.

(Continued)

*Primary Examiner* — Heidi Reese
(74) *Attorney, Agent, or Firm* — Meunier Carlin & Curfman LLC

(57) ABSTRACT

The disclosure relates to Prostaglandin receptor EP2 antagonists, derivatives, compositions, and methods related thereto. In certain embodiments, the disclosure relates to methods of treating or preventing conditions and diseases in which EP2 receptor activation has a physiological role, such as but not limited to, brain injury, inflammatory diseases, neuroinflammation after a seizure, pain, endometriosis, cancer, rheumatoid arthritis, skin inflammation, vascular inflammation, colitis, and neurological disorders by administering a pharmaceutical composition comprising a compound disclosed herein to a subject in need thereof.

6 Claims, 4 Drawing Sheets

(56) References Cited

OTHER PUBLICATIONS

Liang et al. Deletion of the Prostaglandin E2 EP2 Receptor Reduces Oxidative Damage and Amyloid Burden in a Model of Alzheimer's Disease, The Journal of Neuroscience, 2005, 25(44): 10180-10187.
Rojas et al. Inhibition of the prostaglandin EP2 receptor is neuroprotective and accelerates functional recovery in a rat model of organophosphorus induced status epilepticus, Neuropharmacology. Jun. 2015 93: 15-27.
Rojas et al. Inhibition of the prostaglandin E2 receptor EP2 prevents status epilepticus-induced deficits in the novel object recognition task in rats, Neuropharmacology 110 (2016) 419e430.
Silva, A., Mini-Reviews in Medicinal Chemistry, 2005, vol. 5, pp. 893-014.
Yang (2009) Altered hippocampal long-term synaptic plasticity in mice deficient in the PGE2 EP2 receptor. J Neurochem 108:295-304.
Shishido, Yuji, et al. "Synthesis of benzamide derivatives as TRPV1 antagonists." Bioorganic & medicinal chemistry letters 18.3 (2008): 1072-1078.
Database Registry Chem Abstract Service Ohio; database accession No. 749890-20-08, C18H16N6, Benzamide, Abstract.
Supplementary European Search Report issued for Application No. 15785214, dated Sep. 28, 2017.
Extended Supplementary European Search Report issued for Application No. 15785214, dated Oct. 10, 2018.
International Search Report and Written Opinion issued for Application No. PCT/US2015/026364, dated Nov. 5, 2015.
CAPLUS 2008:1508627.
Non-Final Office Action issued for U.S. Appl. No. 16/037,374, dated Apr. 2, 2019.
Notice of Allowance issued for U.S. Appl. No. 16/037,374, dated Aug. 28, 2019.
International Search Report and Written Opinion for International Application No. PCT/2020/023659 dated Jul. 17, 2020.
PubChem, Substance Record for SID 373402298. Available date: May 25, 2018. [retrieved on May 4, 2020]. Retrieved from the Internet: <URL: https://wwwpubchem.ncbi.nih.gov/substance/373402298>.
PubChem, Substance Record for SID 253164928. Available date: Oct. 22, 2015. [retrieved on Jun. 23, 2020]. Retrieved from the Internet: <URL: https://wwwpubchem.ncbi.nih.gov/substance/253164928>.

PROSTAGLANDIN RECEPTOR EP2 ANTAGONISTS, DERIVATIVES, COMPOSITIONS, AND USES RELATED THERETO

CROSS-REFERENCE TO RELATED APPLICATIONS

This application is a division of U.S. application Ser. No. 16/037,374 filed Jul. 17, 2018, which is a continuation of U.S. application Ser. No. 15/307,051 filed Oct. 27, 2016 that granted as U.S. Pat. No. 10,052,332 on Aug. 21, 2018, which is the National Stage of International Application No. PCT/US2015/026364 filed Apr. 17, 2015, which claims the benefit of U.S. Provisional Application No. 61/985,608 filed Apr. 29, 2014. The entirety of each of these applications is hereby incorporated by reference for all purposes.

STATEMENT REGARDING FEDERALLY SPONSORED RESEARCH OR DEVELOPMENT

This invention was made with government support under NS082379 and NS058158 awarded by the National Institutes of Health. The government has certain rights in the invention.

BACKGROUND

Status epilepticus is a condition in which the brain is in a state of persistent seizure. There is evidence that 30-60 minutes of persistent seizure is sufficient to damage neurons and such a seizure is unlikely to self-terminate. Status epilepticus survivors may die soon after or have severe functional impairments accompanied by neuroinflammation. Longer seizure duration, cerebral insult, and refractory convulsive status epilepticus were strongly associated with poor outcomes suggesting a role for early neuroprotective strategies. See Legriel et al., Critical Care Medicine, 2010, 38 (12):2295-2303. Thus, there is a need to identify improved methods for treating or preventing patients recovering from prolonged seizures.

Cyclooxygenase-2 (COX-2), the inducible isoform of COX, is rapidly upregulated in damaged tissue, for example in the central nervous system (CNS) after a seizure or cerebral ischemia. In the CNS, COX-2 induction overall contributes to neuroinflammation and neurodegeneration by producing prostaglandins. In the periphery COX-2 induction has both beneficial and harmful consequences. Pharmacological inhibition of COX can provide relief from the symptoms of inflammation and pain. Current non-steroidal anti-inflammatory drugs (NSAIDs), such as aspirin, ibuprofen, and naproxen, exert their therapeutic effects via nonselectively inhibiting COX. However, multiple downstream COX-2 signaling pathways that promote and oppose tissue injury are complex, which suggests that modulation of a specific prostaglandin receptor could be a superior therapeutic strategy compared with blocking the entire COX-2 cascade.

Prostaglandin E2 ($PGE_2$), a dominant enzymatic product of COX-2 in CNS, can activate four G protein-coupled receptors (GPCRs): EP1, EP2, EP3 and EP4. When activated by $PGE_2$, EP2 stimulates adenylate cyclase (AC) resulting in elevation of cytoplasmic cyclic AMP (cAMP) concentration, which triggers multiple downstream events mediated by protein kinase A (PKA) and exchange protein activated by cAMP (Epac). $PGE_2$/EP2 signaling plays a variety of roles. For example, $PGE_2$ is a major mediator of inflammation and pain. $PGE_2$ is observed as one of the major prostanoid species in inflammatory lesions such as arthritic joints and shows pleiotropic proinflammatory actions in vitro. Therefore, the beneficial effect of NSAIDs could be at least partially if not fully, caused by their inhibition of $PGE_2$ production, and the $PGE_2$/EP2 signaling pathway might induce inflammation actions observed in chronic inflammatory diseases such as rheumatoid arthritis (RA).

$PGE_2$/EP2 signaling regulates UV-induced acute skin inflammation by increasing skin microenviromental blood flow, and EP2 activation by oxidized 1-palmitoyl-2-arachidonoyl-sn-glycero-3-phosphorylcholine (OxPAPC) that might contribute to vascular inflammation. $PGE_2$ signaling through EP2/EP4 exacerbates symptoms of inflammation by increasing IL-23 expression and reducing IL-12/IL-27, which together causes T-cells to differentiate to Th17 effectors both in inflammatory bowel disease (colitis) and arthritis. The $PGE_2$/EP2 system up-regulates a variety of inflammatory mediators including chemokines, cytokines, nitric oxide, prostaglandins, etc., to develop and maintain the inflammatory response.

In the brain, based on the phenotype of EP2 knockout mice, it appears that EP2 activation in microglia promotes inflammation and neurotoxicity in animal models of neurodegenerative diseases including Alzheimer's disease (AD), Parkinson's disease (PD), and amyotrophic lateral sclerosis (ALS). Genetic ablation of EP2 receptor reduced oxidative stress and improved cell survival, accompanied by substantial down-regulation of enzymes in glia that produce reactive oxygen species (ROS), such as inducible nitric oxide synthase (iNOS), COX-2, and NAPDH oxidase. EP2 receptor activation by $PGE_2$ upregulates iNOS/NO expression in activated astrocytes by potentiating the response to inflammatory cytokines like TNF-α and IFN-γ.

Because $PGE_2$/EP2 signaling mediates both peripheral and neural inflammation, pharmacological targeting this pathway can have beneficial implications for the treatment of inflammatory diseases. Thus, there is a need to identify agents that can inhibit $PGE_2$/EP2 signaling.

Buchmann et al., (WO/2008/152099) report compositions for the treatment of disorders connected with the EP2 receptor. See also WO/2012/177618 and WO2010/012396.

SUMMARY

It has been discovered that certain compounds antagonize EP2 signaling. In some embodiments, this disclosure relates to compounds and methods of treating or preventing a related diseases or conditions comprising administering to a subject a therapeutically effective amount of pharmaceutical composition comprising a compound disclosed herein, derivatives, or substituted compounds, e.g., compounds substituted with one or more substitutes including optional salt and prodrug forms. Typically, the compounds display selectivity in inhibiting the EP2 receptor over the EP4 receptor.

The compounds can be combined with one or more pharmaceutically acceptable excipients to form a pharmaceutical composition. Example excipients include diluent, carrier or filler. The compositions can be formulated for enteral, parenteral, topical, transdermal, or pulmonary administration. The compounds can be formulated for immediate release, controlled release, and combinations thereof. Examples of controlled release formulations include delayed release, extended release, pulsatile release, and combinations thereof.

The compounds described herein can be used to treat a variety of diseases or conditions related to a EP2 receptor including, but not limited to, brain injury, neuropathic pain, hypertension, ischemic or hemorrhagic injury, neuroinflammation after a seizure, endometriosis, cancer, inflammatory bowel disease (colitis), arthritis/rheumatoid arthritis, skin inflammation, vascular inflammation, Alzheimer's disease (AD), Parkinson's disease (PD), amyotrophic lateral sclerosis (ALS), kidney disease/transplant rejection, atherosclerosis, ischaemic heart disease, acne vulgaris, asthma, chronic prostatitis, glomerulonephritis, hypersensitivities, pelvic inflammatory disease, sarcoidosis, vasculitis, interstitial cystitis, and autoimmune diseases.

In certain embodiments, compounds described herein can be used to treat or prevent pain, e.g., post surgical pain.

In certain embodiments, the disclosure relates to the use of a compound as described herein in the production of a medicament for the treatment of a disease or condition related to a EP2 receptor. Compounds disclosed here can be contained in pharmaceutical compositions and administered alone or in combination with one or more additional active agents. The active agents can be administered simultaneously in the same dosage form or in separate dosage forms. Alternatively, the active agents can be administered sequentially in different dosage forms.

In certain embodiments, the disclosure relates to method of making compounds disclosed herein by mixing starting materials and reagents disclosed herein under conditions such that the compounds are formed.

DETAILED DESCRIPTION

Figure 1:
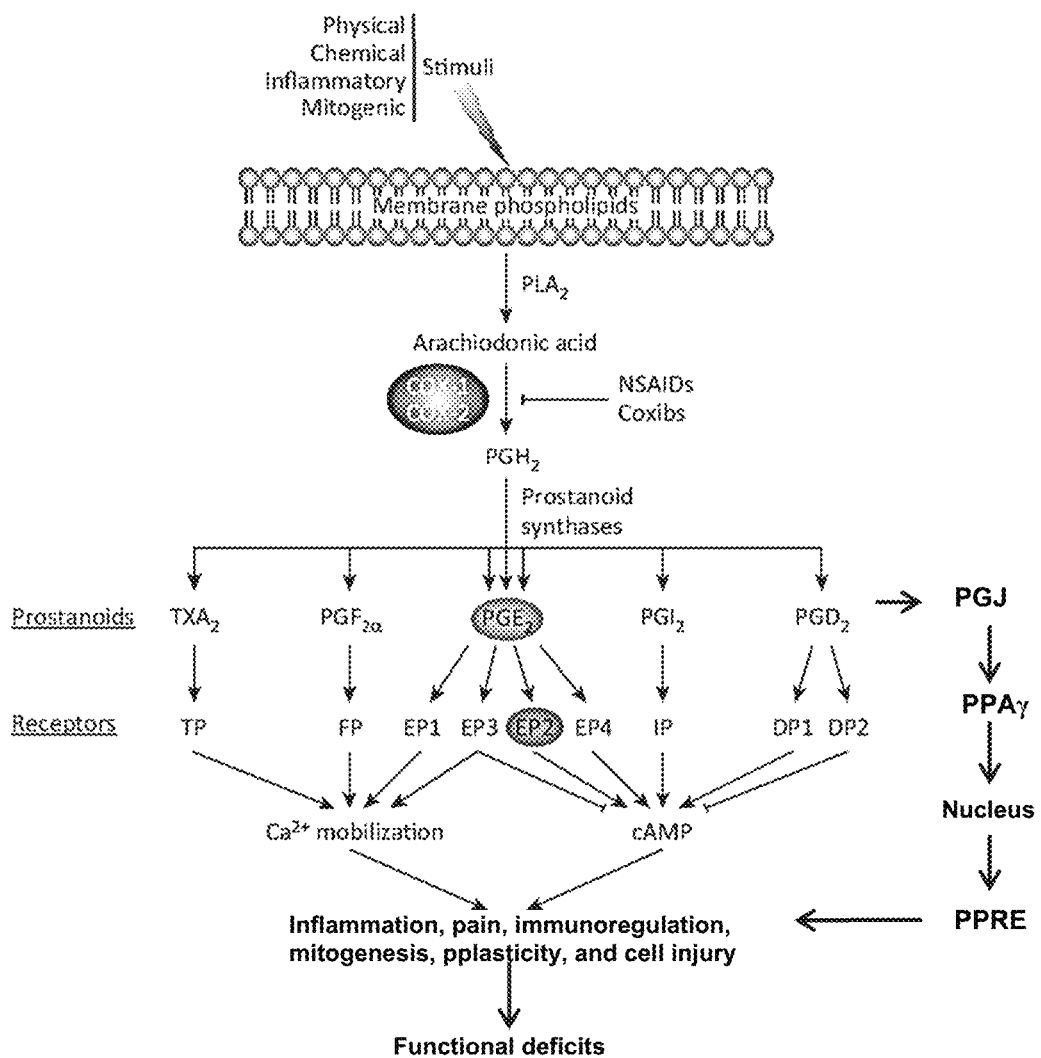
FIG. 1 illustrates the COX-2 signaling pathways. In response to a variety of stimuli, arachiodonic acid (AA) is released from membrane phospholipids by the enzyme phospholipase A2 (PLA2), and then converted to unstable intermediate prostaglandin $H_2$ ($PGH_2$) by cyclooxygenase (COX), which has two forms: COX-1 and COX-2. Most non-steroidal anti-inflammatory drugs (NSAIDs) act as non-selective inhibitors of COX, whereas certain compounds selectively inhibit COX-2. $PGH_2$ is converted to prostanoids by tissue-specific prostanoid synthases. Typically an individual cell will express a limited number of prostanoids and, therefore prostanoids. These bioactive lipids activate a number of membrane-bound G protein-coupled receptors to mediate multiple physiological effects including inflammation, pain, immunoregulation, mitogenesis, plasticity, cell injury, etc., resulting in functional deficits. Nuclear signaling via COX-2 can occur via the PGJ2 metabolite of PGD2 and PPARγ.
Figure 2:
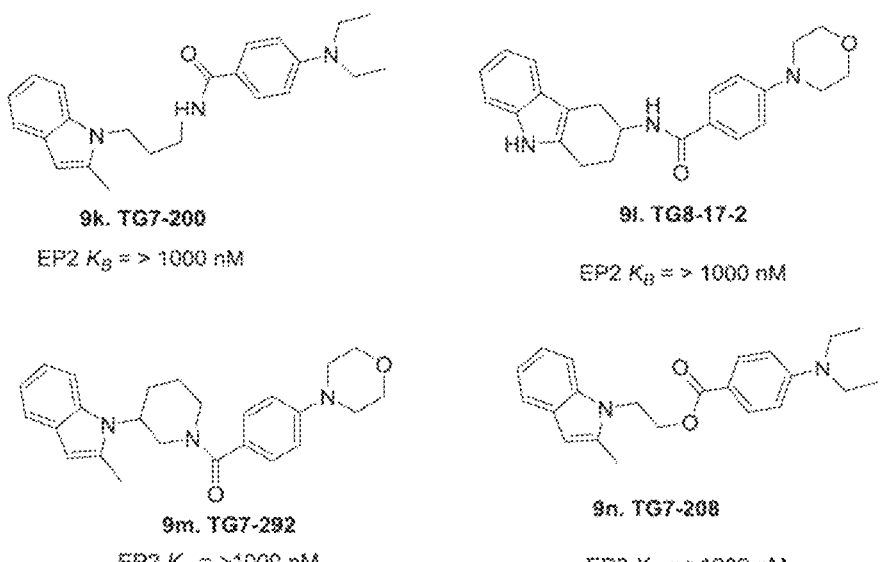
FIG. 2 illustrates certain embodiments of the disclosure.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

Terms

As used herein, "alkyl" means a noncyclic straight chain or branched, unsaturated or saturated hydrocarbon such as those containing from 1 to 10 carbon atoms, typically 1 to 6 carbon atoms. Within any embodiments, herein alkyl may refer to an alkyl with 1 to 6 carbons ($C_{1-6}$alkyl). Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—CH$_3$).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, propoxy, n-butoxy, s-butoxy, t-butoxy.

"Alkylamino" refers an alkyl group as defined above attached through an amino bridge. An example of an alkylamino is methylamino, (i.e., —NH—CH$_3$).

"Alkanoyl" refers to an alkyl as defined above attached through a carbonyl bride (i.e., —(C=O)alkyl).

"Alkyloxycarbonyl" refers to an alkyl as defined above attached through a carboxy bridge (i.e., —(C=O)Oalkyl. "Alkylcarbamoyl" refers to an alkyl as defined above attached through a carbonyl bridge (i.e., —(C=O)NHalkyl).

"Alkanoyl" refers to an alkyl as defined above attached through a carbonyl bridge (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfonamide" refers to an alkyl as defined above attached through a sulfamoyl bridge (i.e., —S(=O)$_2$NHalkyl), and an "Arylsulfonamide" refers to an alkyl attached through a sulfamoyl bridge (i.e., (i.e., —S(=O)$_2$NHaryl).

"Alkylsulfinyl" refers to an alkyl as defined attached through a sulfinyl bridge (i.e. —S(=O)alkyl).

The terms "halogen" and "halo" refer to fluorine, chlorine, bromine, and iodine.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NR$_a$R$_b$, —NR$_a$C(=O)R$_b$, —NR$_a$C(=O)NR$_a$NR$_b$, —NR$_a$C(=O)OR$_b$, —NR$_a$SO$_2$R$_b$, —C(=O)R$_a$, —C(=O)OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$ and —S(=O)$_2$OR$_a$. R$_a$ and R$_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing a oxygen atom with a sulfur atom or replacing a amino group with a hydroxyl group. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

Prostaglandin Receptor EP2 Antagonists/Inhibitors

Certain compounds were identified as antagonists of the human EP2 receptor. Although it is not intended that certain embodiments of the disclosure be limited by any specific mechanism, certain of these compounds have low cellular toxicity and represent competitive antagonists of the EP2 prostaglandin receptor.

In certain embodiments, contemplated compounds are of Formula I,

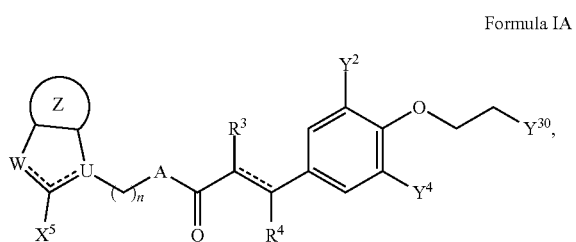

Formula IA or pharmaceutically acceptable salt, ester, or prodrug thereof, wherein:

a broken line represents a single or double bond;

A is $NR^5$, $CR^6R^7$, O, or S;

if there is a double bond between U and the attached carbon, then U is C; or if there is a single bond between U and the attached carbon, then U is N;

if there is a double bond between W and the attached carbon, then W is $CX^6$; or if there is a single bond between W and the attached carbon, then W is $NX^6$;

Z is a 5 to 7 membered carbocyclyl, aryl, or heterocyclyl wherein Z is optionally substituted;

n is 1, 2, 3, or 4;

$R^3$, $R^4$, $R^5$, $R^6$, and $R^7$, are each, the same or different, hydrogen or alkyl, wherein $R^3$, $R^4$, $R^5$, $R^6$, and $R^7$, are optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein 10 is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;

$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^5$ and $X^6$ are each, the same or different, hydrogen or alkyl, wherein $X^5$ and $X^6$ are optionally substituted with one or more, the same or different, V;

$V^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

$Y^2$ and $Y^4$ are each, the same or different, hydrogen, 2-hydroxyethoxy, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^2$ and $Y^4$ are optionally substituted with one or more, the same or different, $Y^{10}$;

$Y^{10}$ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $Y^{10}$ is optionally substituted with one or more, the same or different, $Y^{11}$;

$Y^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$Y^{30}$ is hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $Y^{30}$ is optionally substituted with one or more, the same or different, $Y^{31}$;

$Y^{31}$ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $Y^{31}$ is optionally substituted with one or more, the same or different, $Y^{32}$; and $Y^{32}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $Y^{30}$ is hydroxy optionally substituted.

In certain embodiments, contemplated compounds have Formula IA,

Formula IA

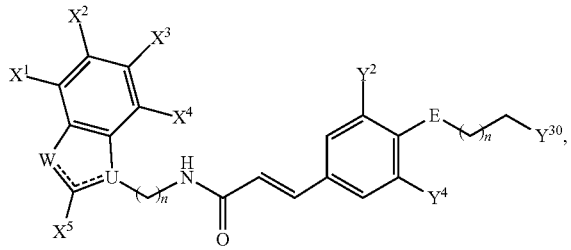

or pharmaceutically acceptable salt or prodrug thereof, wherein:

a broken line represents a single or double bond; m is 1, 2, 3, or 4; n is 1, 2, 3, or 4; E is NH, S, or O;

if there is a double bond between U and the attached carbon, then U is C; or if there is a single bond between U and the attached carbon, then U is N;

if there is a double bond between W and the attached carbon, then W is $CX^6$; or if there is a single bond between W and the attached carbon, then W is $NX^6$;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

$Y^2$ and $Y^4$ are each, the same or different, hydrogen, 2-hydroxyethoxy, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $Y^2$ and $Y^4$ are optionally substituted with one or more, the same or different, $Y^{10}$;

$V^{10}$ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $Y^{10}$ is optionally substituted with one or more, the same or different, $Y^{11}$;

$Y^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$Y^{30}$ is hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $Y^{30}$ is optionally substituted with one or more, the same or different, $Y^{31}$;

$Y^{31}$ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $Y^{31}$ is optionally substituted with one or more, the same or different, $Y^{32}$; and $Y^{32}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, n is 2. In certain embodiments, W is N and U is $CX^5$ and $X^5$ is alkyl. In certain embodiments, W is $CX^6$ and U is N and $X^5$ is alkyl optionally substituted.

In certain embodiments, $Y^{30}$ is hydroxy, amino, alkylamino, (alkyl)$_2$amino or heterocyclyl optionally substituted.

In certain embodiments, $Y^2$ is 2-hydroxyethoxy optionally substituted. In certain embodiments, $Y^4$ is 2-hydroxyethoxy optionally substituted.

In certain embodiments, $X^5$ is methyl optionally substituted with one or more halogen.

In certain embodiments, compounds have Formula II,

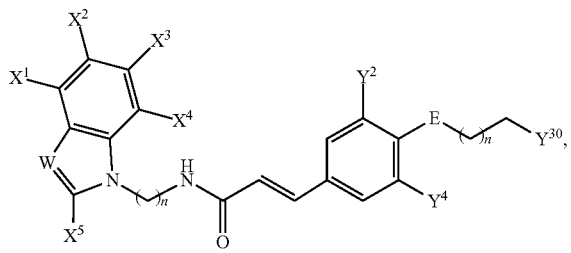

Formula II or pharmaceutically acceptable salt or prodrug thereof, wherein:

m is 1, 2, 3, or 4; n is 1, 2, 3, or 4; E is NH, S, or O; W is $CX^6$ or N;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl $Y^2$ and $Y^4$ are each, the same or different, hydrogen, 2-hydroxyethoxy, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^2$ and $Y^4$ are optionally substituted with one or more, the same or different, $Y^{10}$;

$Y^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{10}$ is optionally substituted with one or more, the same or different, $Y^{11}$;

$Y^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$Y^{30}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{30}$ is optionally substituted with one or more, the same or different, $Y^{31}$;

$Y^{31}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{31}$ is optionally substituted with one or more, the same or different, $Y^{32}$; and $Y^{32}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds have Formula III,

Formula III

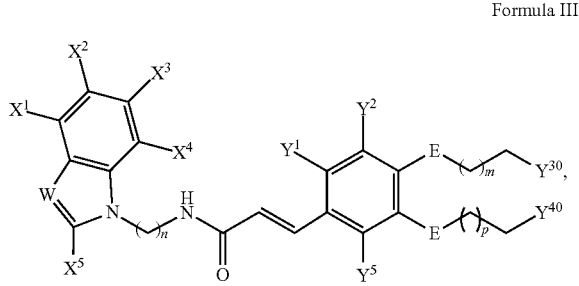

or pharmaceutically acceptable salt or prodrug thereof, wherein:

m is 1, 2, 3, or 4; n is 1, 2, 3, or 4; p is 1, 2, 3, or 4; E is NH, S, or O; W is $CX^6$ or N;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl $Y^1$, $Y^2$, and $Y^5$ are each, the same or different, hydrogen, 2-hydroxyethoxy, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^1$, $Y^2$, and $Y^5$ are optionally substituted with one or more, the same or different, $Y^{11}$;

$Y^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{10}$ is optionally substituted with one or more, the same or different, $Y^{11}$;

$Y^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$Y^{30}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{30}$ is optionally substituted with one or more, the same or different, $Y^{31}$;

$Y^{31}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{31}$ is optionally substituted with one or more, the same or different, $Y^{32}$;

$Y^{32}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$Y^{40}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{40}$ is optionally substituted with one or more, the same or different, $Y^{41}$;

$Y^{41}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{41}$ is optionally substituted with one or more, the same or different, $Y^{42}$; and $Y^{42}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, n is 2. In certain embodiments, W is NH.

In certain embodiments, compounds have Formula IV,

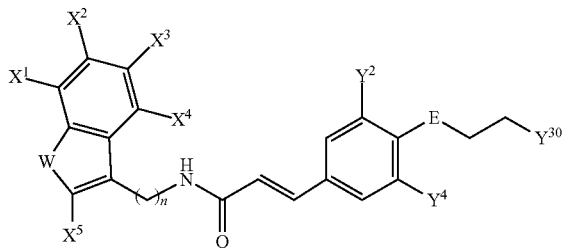

Formula IV or pharmaceutically acceptable salt or prodrug thereof, wherein:

n is 1, 2, 3, or 4; E is NH, S, or O; W is $NX^6$ or 0;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl $Y^2$ and $Y^4$ are each, the same or different, hydrogen, 2-hydroxyethoxy, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^2$ and $Y^4$ are optionally substituted with one or more, the same or different, $Y^{10}$;

$Y^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{10}$ is optionally substituted with one or more, the same or different, $Y^{11}$;

$Y^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$Y^{30}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{30}$ is optionally substituted with one or more, the same or different, $Y^{31}$;

$Y^{31}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{31}$ is optionally substituted with one or more, the same or different, $Y^{32}$; and $Y^{32}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, n is 2. In certain embodiments, W is NH.

In certain embodiments, compounds have Formula V,

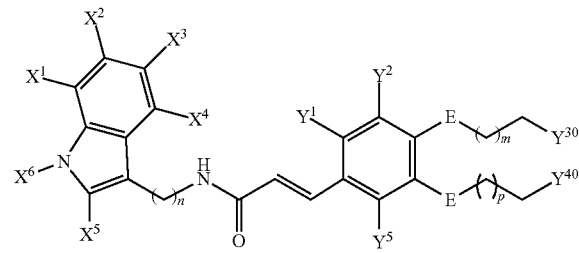

Formula V or pharmaceutically acceptable salt or prodrug thereof, wherein:

m is 1, 2, 3, or 4; n is 1, 2, 3, or 4; p is 1, 2, 3, or 4; E is NH, S, or O;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl $Y^1$, $Y^2$, and $Y^5$ are each, the same or different, hydrogen, 2-hydroxyethoxy, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^1$, $Y^2$, and $Y^5$ are optionally substituted with one or more, the same or different, $Y^{10}$;

$Y^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{10}$ is optionally substituted with one or more, the same or different, $Y^{11}$;

$Y^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$Y^{30}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{30}$ is optionally substituted with one or more, the same or different, $Y^{31}$;

$Y^{31}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{31}$ is optionally substituted with one or more, the same or different, $Y^{32}$;

$Y^{32}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$Y^{40}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{40}$ is optionally substituted with one or more, the same or different, $Y^{41}$;

$Y^{41}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{41}$ is optionally substituted with one or more, the same or different, $Y^{42}$; and $Y^{42}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds have Formula VI,

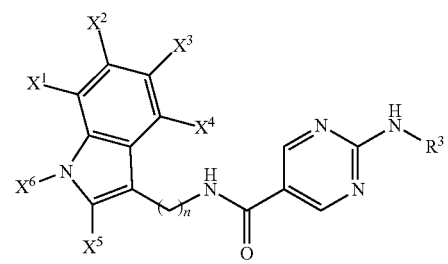

Formula VI or pharmaceutically acceptable salt or prodrug thereof, wherein:

n is 1, 2, 3, or 4;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^3$ is hydrogen, alkyl, formyl, carbamoyl, alkylsulfinyl, alkylsulfonyl, arylsulfonyl, carbocyclyl, aryl, or heterocyclyl, wherein $R^3$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiment, $R^3$ is aryl or heterocyclyl optionally substituted.

In certain embodiments, compounds have Formula VII,

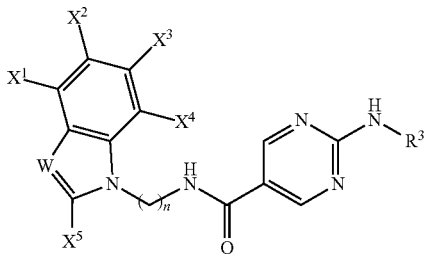

Formula VII or pharmaceutically acceptable salt or prodrug thereof, wherein:

n is 1, 2, 3, or 4; W is $CX^6$ or N;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^3$ is hydrogen, alkyl, formyl, carbamoyl, alkylsulfinyl, alkylsulfonyl, arylsulfonyl, carbocyclyl, aryl, or heterocyclyl, wherein $R^3$ is optionally substituted with one or more, the same or different, V;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiment, $R^3$ is aryl or heterocyclyl optionally substituted.

In certain embodiments, compounds have Formula VIII,

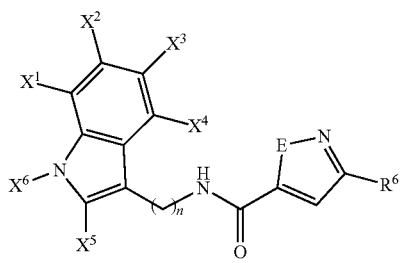

Formula VIII or pharmaceutically acceptable salt or prodrug thereof, wherein:

n is 1, 2, 3, or 4; E is NH, S, or O;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^6$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds have Formula IX,

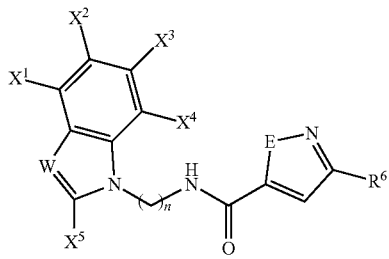

Formula IX or pharmaceutically acceptable salt or prodrug thereof, wherein:

n is 1, 2, 3, or 4; E is NH, S, or O; W is $CX^6$ or N;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^6$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds have Formula X,

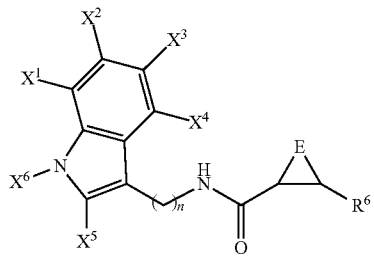

Formula X or pharmaceutically acceptable salt or prodrug thereof, wherein:

n is 1, 2, 3, or 4; E is NH, S, or O;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^6$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^6$ is phenyl.

In certain embodiments, compounds of Formula V have Formula XI,

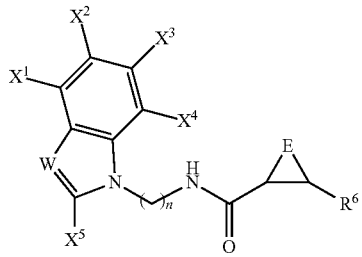

Formula XI or pharmaceutically acceptable salt or prodrug thereof, wherein:

n is 1, 2, 3, or 4; E is NH, S, or O; W is $CX^6$ or N; $X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^6$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^6$ is phenyl.

In certain embodiments, compounds of Formula VI have Formula XII,

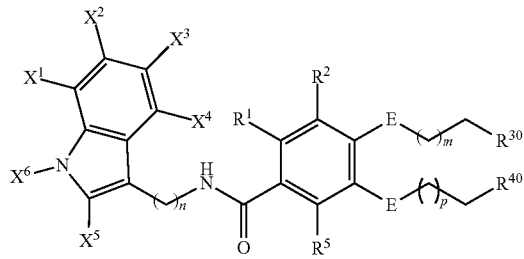

Formula XII or pharmaceutically acceptable salt or prodrug thereof, wherein:

m is 1, 2, 3, or 4; n is 1, 2, 3, or 4; p is 1, 2, 3, or 4; E is NH, S, or O;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^1$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^1$, $R^2$, and $R^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, and $R^5$ are optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{30}$ and $R^{40}$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{30}$ and $R^{40}$ are optionally substituted with one or more, the same or different, $R^{100}$;

$R^{100}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{100}$ is optionally substituted with one or more, the same or different, $R^{101}$;

$R^{101}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{100}$ is optionally substituted with one or more, the same or different, $R^{102}$;

$R^{102}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds of Formula VI have Formula XIII,

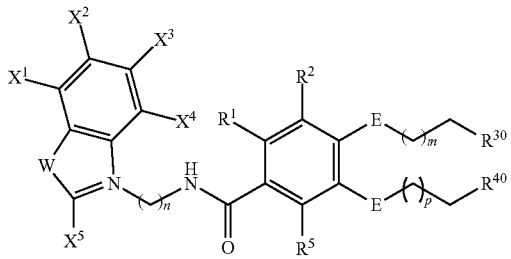

Formula XIII or pharmaceutically acceptable salt or prodrug thereof, wherein:

m is 1, 2, 3, or 4; n is 1, 2, 3, or 4; p is 1, 2, 3, or 4; E is NH, S, or O; W is $CX^6$ or N;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^1$, $R^2$, and $R^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, and $R^5$ are optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{30}$ and $R^{40}$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{30}$ and $R^{40}$ are optionally substituted with one or more, the same or different, $R^{100}$;

$R^{100}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{100}$ is optionally substituted with one or more, the same or different, $R^{101}$;

$R^{101}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{101}$ is optionally substituted with one or more, the same or different, $R^{102}$;

$R^{102}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, contemplated compounds have Formula XIV,

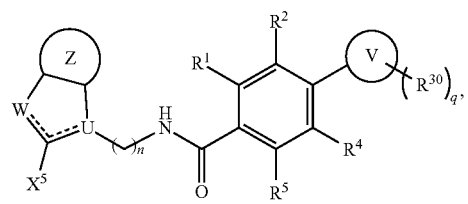

Formula XIV or pharmaceutically acceptable salt or prodrug thereof, wherein:

a broken line represents the presence of a single or double bond;

n is 1, 2, 3, or 4; q is 0, 1 or 2;

if there is a double bond between U and the attached carbon, then U is C; or if there is a single bond between U and the attached carbon, then U is N;

if there is a double bond between W and the attached carbon, then W is $CX^6$; or if there is a single bond between W and the attached carbon, then W is $NX^6$;

V is a 5 or 6 membered heterocyclyl having at least one nitrogen heteroatom;

Z is a 5 to 7 membered carbocyclyl, aryl, or heterocyclyl optionally substituted;

$R^1$, $R^2$, $R^4$, and $R^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, $R^4$, and $R^5$ are optionally substituted with one or more, the same or different, $R^{10}$;

R¹⁰ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R¹⁰ is optionally substituted with one or more, the same or different, R¹¹;

R¹¹ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R¹¹ is optionally substituted with one or more, the same or different, R¹²;

R¹² is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

R³⁰ is at each occurance, the same or different, hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R³⁰ is optionally substituted with one or more, the same or different, R¹⁰⁰;

R¹⁰⁰ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R¹⁰⁰ is optionally substituted with one or more, the same or different, R¹⁰¹;

R¹⁰¹ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R¹⁰¹ is optionally substituted with one or more, the same or different, R¹⁰²;

R¹⁰² is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

X⁵ and X⁶ are each, the same or different, hydrogen or alkyl, wherein X⁵ and X⁶ are optionally substituted with one or more, the same or different, X¹⁰;

X¹⁰ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein X¹⁰ is optionally substituted with one or more, the same or different, X¹¹; and X¹¹ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the V ring is a diazolyl, triazolyl, or tetrazolyl.

In certain embodiments, compounds of Formula XIV have Formula XIVA,

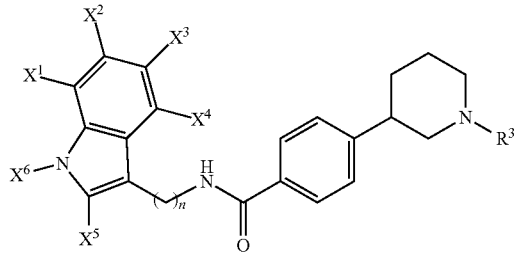

Formula XIVA or pharmaceutically acceptable salt or prodrug thereof, wherein:

n is 1, 2, 3, or 4;

X¹, X², X³, and X⁴ are each, the same or different, hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein X¹, X², X³, and X⁴ are optionally substituted with one or more, the same or different, X¹⁰;

X⁵ and X⁶ are each, the same or different, hydrogen or alkyl, wherein X⁵ and X⁶ are optionally substituted with one or more, the same or different, X¹⁰;

X¹⁰ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein X¹⁰ is optionally substituted with one or more, the same or different, X¹¹;

X¹¹ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

R³ is hydrogen, alkyl, formyl, carbamoyl, alkylsulfinyl, alkylsulfonyl, arylsulfonyl, carbocyclyl, aryl, or heterocyclyl, wherein R³ is optionally substituted with one or more, the same or different, R¹⁰;

R¹⁰ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R¹⁰ is optionally substituted with one or more, the same or different, R¹¹;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds of Formula XIV have Formula XIVB,

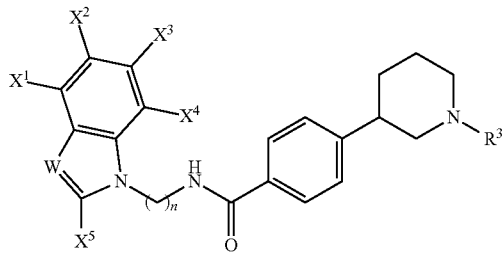

Formula XIVB or pharmaceutically acceptable salt or prodrug thereof, wherein:

n is 1, 2, 3, or 4; W is $CX^6$ or N;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^3$ is hydrogen, alkyl, formyl, carbamoyl, alkylsulfinyl, alkylsulfonyl, arylsulfonyl, carbocyclyl, aryl, or heterocyclyl, wherein $R^3$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds of Formula XIV have Formula XIVC,

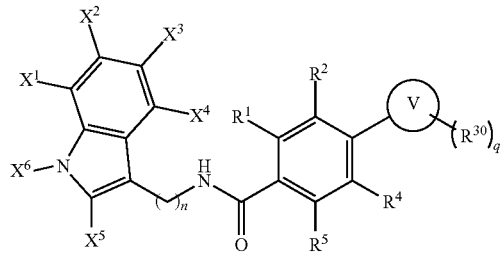

Formula XIVC or pharmaceutically acceptable salt or prodrug thereof, wherein:

n is 1, 2, 3, or 4; q is 0, 1 or 2;

V is a 5 or 6 membered heterocyclyl having at least one nitrogen heteroatom;

$R^1$, $R^2$, $R^4$, and $R^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, $R^4$, and $R^5$ are optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{30}$ is at each occurance, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{30}$ is optionally substituted with one or more, the same or different, $R^{100}$;

$R^{100}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{100}$ is optionally substituted with one or more, the same or different, $R^{101}$;

$R^{101}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{101}$ is optionally substituted with one or more, the same or different, $R^{102}$;

$R^{102}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds of Formula XIV have Formula XIVD,

Formula XIVD

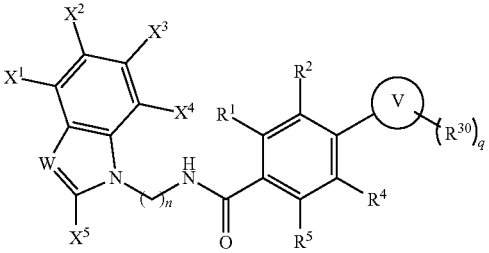

or pharmaceutically acceptable salt or prodrug thereof, wherein:

n is 1, 2, 3, or 4; q is 0, 1 or 2; W is $CX^6$ or N;

V is a 5 or 6 membered heterocyclyl having at least one nitrogen heteroatom;

$R^1$, $R^2$, $R^4$, and $R^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, $R^4$, and $R^5$ are optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{30}$ is at each occurance, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{30}$ is optionally substituted with one or more, the same or different, $R^{100}$;

$R^{100}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{100}$ is optionally substituted with one or more, the same or different, R$^{101}$;

R$^{101}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{101}$ is optionally substituted with one or more, the same or different, R$^{102}$;

R$^{102}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

X$^1$, X$^2$, X$^3$, and X$^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein X$^1$, X$^2$, X$^3$, and X$^4$ are optionally substituted with one or more, the same or different, X$^{10}$;

X$^5$ and X$^6$ are each, the same or different, hydrogen or alkyl, wherein X$^5$ and X$^6$ are optionally substituted with one or more, the same or different, X$^{10}$;

X$^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein X$^{10}$ is optionally substituted with one or more, the same or different, X$^{11}$;

X$^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds of Formula XIV have Formula XIVE,

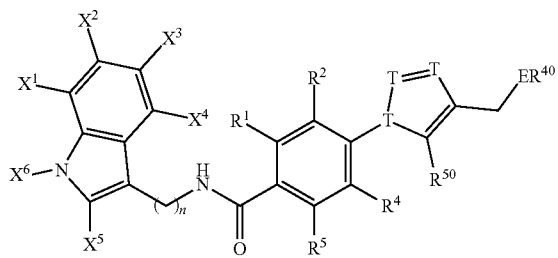

Formula XIVE or pharmaceutically acceptable salt or prodrug thereof, wherein:

n is 1, 2, 3, or 4; E is NH, S, or O;

T is at each occurrence, the same or different, N or CH;

R$^1$, R$^2$, R$^4$, and R$^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^1$, R$^2$, R$^4$, and R$^5$ are optionally substituted with one or more, the same or different, R$^{10}$;

R$^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{10}$ is optionally substituted with one or more, the same or different, R$^{11}$;

R$^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{11}$ is optionally substituted with one or more, the same or different, R$^{12}$;

R$^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

R$^{40}$ and R$^{50}$ are at each occurance, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{40}$ and R$^{50}$ are optionally substituted with one or more, the same or different, R$^{100}$;

R$^{100}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{100}$ is optionally substituted with one or more, the same or different, R$^{101}$;

R$^{101}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{101}$ is optionally substituted with one or more, the same or different, R$^{102}$;

R$^{102}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds of Formula XIV have Formula XIVF,

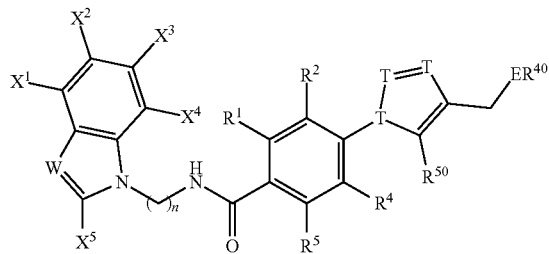

Formula XIVF or pharmaceutically acceptable salt or prodrug thereof, wherein:

n is 1, 2, 3, or 4; E is NH, S, or O; T is at each occurrence, the same or different, N or CH;

W is $CX^6$ or N;

$R^1$, $R^2$, $R^4$, and $R^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, $R^4$, and $R^5$ are optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{40}$ and $R^{50}$ are at each occurance, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{40}$ and $R^{50}$ are optionally substituted with one or more, the same or different, $R^{100}$;

$R^{100}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{100}$ is optionally substituted with one or more, the same or different, $R^{101}$;

$R^{101}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{101}$ is optionally substituted with one or more, the same or different, $R^{102}$;

$R^{102}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds of Formula XIV have Formula XIVG,

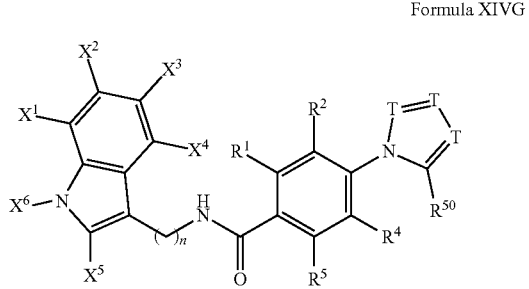

Formula XIVG or pharmaceutically acceptable salt or prodrug thereof, wherein:

n is 1, 2, 3, or 4; T is at each occurrence, the same or different, N or CH;

$R^1$, $R^2$, $R^4$, and $R^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, $R^4$, and $R^5$ are optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{50}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{50}$ is optionally substituted with one or more, the same or different, $R^{100}$;

$R^{100}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{100}$ is optionally substituted with one or more, the same or different, $R^{101}$;

$R^{101}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{101}$ is optionally substituted with one or more, the same or different, $R^{102}$;

$R^{102}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$; $X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds of Formula XIV have Formula XIVH,

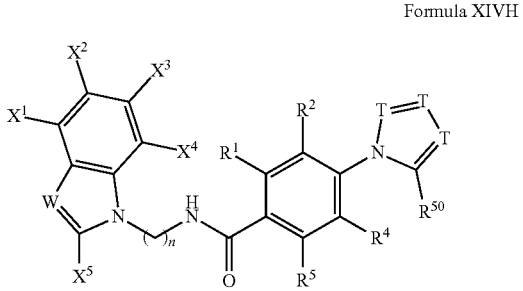

Formula XIVH or pharmaceutically acceptable salt or prodrug thereof, wherein:

n is 1, 2, 3, or 4; T is at each occurrence, the same or different, N or CH; W is $CX^6$ or N;

$R^1$, $R^2$, $R^4$, and $R^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, $R^4$, and $R^5$ are optionally substituted with one or more, the same or different, $R^0$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{50}$ is at each occurance, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{50}$ is optionally substituted with one or more, the same or different, $R^{100}$;

$R^{100}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{100}$ is optionally substituted with one or more, the same or different, $R^{101}$;

$R^{01}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{101}$ is optionally substituted with one or more, the same or different, $R^{102}$;

$R^{102}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds of Formula XIV have Formula XIVJ,

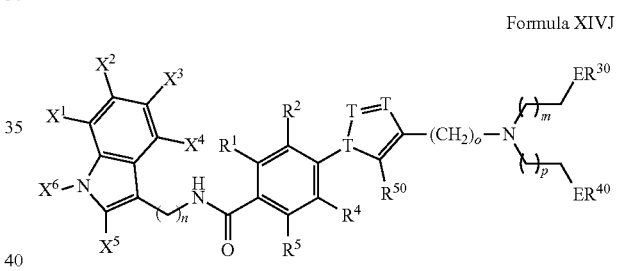

Formula XIVJ or pharmaceutically acceptable salt or prodrug thereof, wherein:

m is 1, 2, 3, or 4; n is 1, 2, 3, or 4; o is 1, 2, 3, or 4; p is 1, 2, 3, or 4; E is NH, S, or O;

T is at each occurrence, the same or different, N or CH;

$R^1$, $R^2$, $R^4$, and $R^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, $R^4$, and $R^5$ are optionally substituted with one or more, the same or different, $R^0$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{30}$, $R^{40}$, and $R^{50}$ are at each occurance, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{30}$, $R^{40}$, and $R^{50}$ are optionally substituted with one or more, the same or different, $R^{100}$;

$R^{100}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{100}$ is optionally substituted with one or more, the same or different, $R^{101}$;

$R^{101}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{101}$ is optionally substituted with one or more, the same or different, $R^{102}$;

$R^{102}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds of Formula XIV have Formula XIVK,

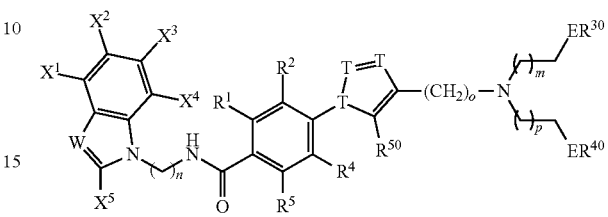

Formula XIVK or pharmaceutically acceptable salt or prodrug thereof, wherein:

m is 1, 2, 3, or 4; n is 1, 2, 3, or 4; o is 1, 2, 3, or 4; p is 1, 2, 3, or 4; E is NH, S, or O;

T is at each occurrence, the same or different, N or CH;

W is $CX^6$ or N;

$R^1$, $R^2$, $R^4$, and $R^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, $R^4$, and $R^5$ are optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{30}$, $R^{40}$, and $R^{50}$ are at each occurance, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{30}$, $R^{40}$, and $R^{50}$ are optionally substituted with one or more, the same or different, $R^{100}$;

$R^{101}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{100}$ is optionally substituted with one or more, the same or different, $R^{101}$;

$R^{101}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{101}$ is optionally substituted with one or more, the same or different, $R^{102}$;

$R^{102}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds of Formula XIV have Formula XIVL,

Formula XIVL

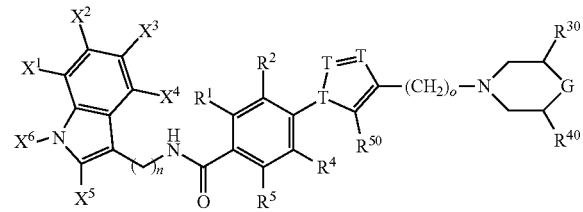

or pharmaceutically acceptable salt or prodrug thereof, wherein:

n is 1, 2, 3, or 4; o is 1, 2, 3, or 4; G is O, NH, or CH$_2$;

T is at each occurrence, the same or different, N or CH;

$R^1$, $R^2$, $R^4$, and $R^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, $R^4$, and $R^5$ are optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{30}$, $R^{40}$, and $R^{50}$ are at each occurance, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{30}$, $R^{40}$, and $R^{50}$ are optionally substituted with one or more, the same or different, $R^{100}$;

$R^{100}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{100}$ is optionally substituted with one or more, the same or different, $R^{101}$;

$R^{101}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{101}$ is optionally substituted with one or more, the same or different, $R^{102}$;

$R^{102}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds of Formula XIV have Formula XIVM,

Formula XIVM

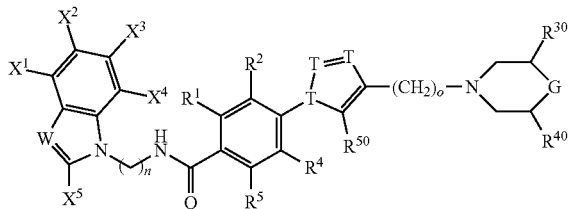

or pharmaceutically acceptable salt or prodrug thereof, wherein:

n is 1, 2, 3, or 4; o is 1, 2, 3, or 4; G is O, NH, or CH$_2$;

T is at each occurrence, the same or different, N or CH;

W is CX$^6$ or N;

$R^1$, $R^2$, $R^4$, and $R^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, $R^4$, and $R^5$ are optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{30}$, $R^{40}$, and $R^{50}$ are at each occurance, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{30}$, $R^{40}$, and $R^{50}$ are optionally substituted with one or more, the same or different, $R^{100}$;

$R^{100}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{100}$ is optionally substituted with one or more, the same or different, $R^{101}$;

$R^{101}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{101}$ is optionally substituted with one or more, the same or different, $R^{102}$;

$R^{102}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds of Formula XIV have Formula XIVN,

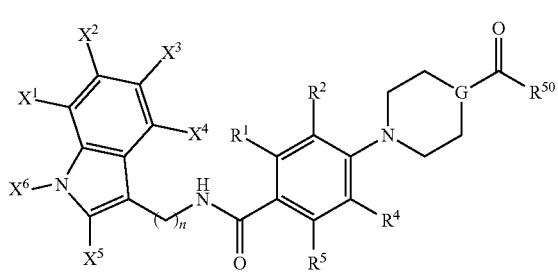

Formula XIVN or pharmaceutically acceptable salt or prodrug thereof, wherein:

n is 1, 2, 3, or 4; G is N or CH;

$R^1$, $R^2$, $R^4$, and $R^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, $R^4$, and $R^5$ are optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^2$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{50}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{50}$ is optionally substituted with one or more, the same or different, $R^{100}$;

$R^{100}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{100}$ is optionally substituted with one or more, the same or different, $R^{101}$;

$R^{101}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{101}$ is optionally substituted with one or more, the same or different, $R^{102}$;

$R^{102}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^{50}$ is piperazinyl or 2-(dimethylamino)ethyl-1-amino optionally substituted.

In certain embodiments, compounds of Formula XIV have Formula XIVO,

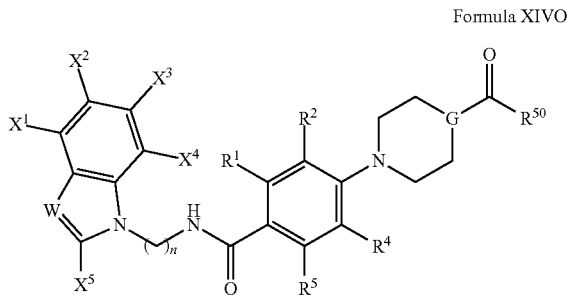

Formula XIVO or pharmaceutically acceptable salt or prodrug thereof, wherein:

n is 1, 2, 3, or 4; G is N or CH; W is $CX^6$ or N;

$R^1$, $R^2$, $R^4$, and $R^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^1$, R$^2$, R$^4$, and R$^5$ are optionally substituted with one or more, the same or different, R$^{10}$;

R$^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{10}$ is optionally substituted with one or more, the same or different, R$^{11}$;

R$^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^1$ is optionally substituted with one or more, the same or different, R$^{12}$;

R$^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

R$^{50}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{50}$ is optionally substituted with one or more, the same or different, R$^{100}$;

R$^{100}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{100}$ is optionally substituted with one or more, the same or different, R$^{101}$;

R$^{101}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{101}$ is optionally substituted with one or more, the same or different, R$^{102}$;

R$^{102}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

X$^1$, X$^2$, X$^3$, and X$^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein X$^1$, X$^2$, X$^3$, and X$^4$ are optionally substituted with one or more, the same or different, XV;

X$^5$ and X$^6$ are each, the same or different, hydrogen or alkyl, wherein X$^5$ and X$^6$ are optionally substituted with one or more, the same or different, X$^{10}$;

X$^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein X$^{10}$ is optionally substituted with one or more, the same or different, X$^{11}$;

X$^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds of Formula XIV have Formula XIVP,

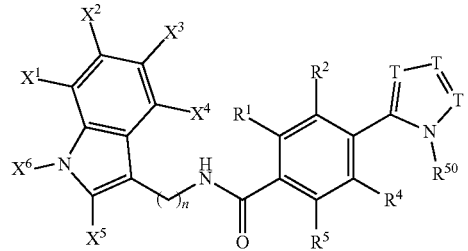

Formula XIVP or pharmaceutically acceptable salt or prodrug thereof, wherein:

n is 1, 2, 3, or 4; T is at each occurrence, the same or different, N or CH;

R$^1$, R$^2$, R$^4$, and R$^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^1$, R$^2$, R$^4$, and R$^5$ are optionally substituted with one or more, the same or different, R$^{10}$;

R$^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{10}$ is optionally substituted with one or more, the same or different, R$^{11}$;

R$^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{11}$ is optionally substituted with one or more, the same or different, R$^{12}$;

R$^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N- diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{50}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{50}$ is optionally substituted with one or more, the same or different, $R^{100}$;

$R^{100}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{100}$ is optionally substituted with one or more, the same or different, $R^{101}$;

$R^{101}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{101}$ is optionally substituted with one or more, the same or different, $R^{102}$;

$R^{102}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$; $X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds of Formula XIV have Formula XIVQ,

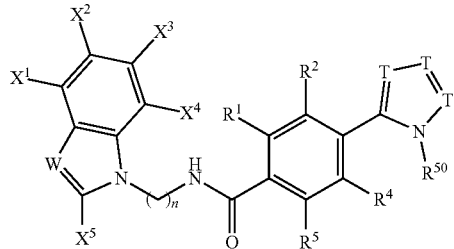

Formula XIVQ or pharmaceutically acceptable salt or prodrug thereof, wherein:

n is 1, 2, 3, or 4; T is at each occurrence, the same or different, N or CH; W is $CX^6$ or N;

$R^1$, $R^2$, $R^4$, and $R^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, $R^4$, and $R^5$ are optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{50}$ is at each occurance, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{50}$ is optionally substituted with one or more, the same or different, $R^{100}$;

$R^{100}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{100}$ is optionally substituted with one or more, the same or different, $R^{101}$;

$R^{101}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{101}$ is optionally substituted with one or more, the same or different, $R^{102}$;

$R^{102}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

Prostaglandin Receptor EP2 Related Diseases and Conditions

Prostaglandin EP2 receptor related diseases or conditions include neurological disorders, brain injury, neuropathic pain, hypertension, ischemic injury, neuroinflamation after a seizure, endometriosis, cancer, inflammatory bowel disease (colitis), arthritis/rheumatoid arthritis, skin inflammation, vascular inflammation, Alzheimer's disease (AD), Parkinson's disease (PD), and amyotrophic lateral sclerosis (ALS), kidney disease/transplant rejection, atherosclerosis, ischaemic heart disease, acne vulgaris, asthma, chronic prostatitis, glomerulonephritis, hypersensitivities, inflammatory bowel diseases, pelvic inflammatory disease, sarcoidosis, vasculitis, interstitial cystitis, and other autoimmune diseases.

Neurological disorders, diseases, or conditions contemplated include, brain injury such as brain damage according to cerebral lobe, basal ganglia, cerebellum, brainstem, frontal lobe damage, parietal lobe damage, temporal lobe damage, occipital lobe damage, aphasia, dysarthria, apraxia, agnosia, amnesia, spinal cord disorders, peripheral nervous system disorders, cranial nerve disorders, autonomic nervous system disorders, seizure disorders such as epilepsy, movement disorders such as Parkinson's disease, sleep disorders, headaches (including migraine), lower back and neck pain, neuropathic pain, delirium and dementia such as in Alzheimer's disease, dizziness, vertigo, stupor, coma, stroke (CVA, cerebrovascular attack), multiple sclerosis (MS) and other demyelinating diseases, infections of the brain or spinal cord (including meningitis), prion diseases, and complex regional pain syndrome (CRPS).

Status epilepticus refers to a potentially life-threatening condition in which the brain is in a state of persistent seizure or recurrent seizure typically lasting longer than about 20-30 minutes. It is not intended that time of the seizure be of any specific duration, but typically 30-60 minutes is sufficient to damage neurons and that seizures are unlikely to self-terminate by that time. The mortality rate of status epilepticus is high, especially if treatment is not initiated soon after.

In certain embodiments, the compounds or compositions are administered at about 0.5, 1, 2, 3, 4, or 5 hours after a subject has stopped having a seizure, e.g., because the subject was administered an anticonvulsant or an anesthetic.

Examples of why one may experience such a seizure include because they have epilepsy and have stopped taking anticonvulsant medication, a stroke, hemorrhage, or as a result of intoxicants, adverse reactions to drugs, consumption of alcoholic beverages, fasting, trauma to the brain, brain disorders such as, but not limited to, meningitis, encephalitis, brain tumors, abscess. It is contemplated that in certain embodiments, the subject may be in a convulsive status epilepticus for any of the reseasons provided herein.

Status epilepticus may be treated with midazolam, valproate, phenobarbital, thiopental pentobarbital, diazepam or other benzodiazepines such as clonazepam, or lorazepam. If these compounds are ineffective one may administer general anesthetics such as propofol or an NMDA antagonist such as ketamine. In certain embodiments, the disclosure contemplates administering compounds disclosed herein after or in combination with being treated with anticonvulsive agents such as those describe above.

COX-2 and prostanoid products have a role in progression of tumors including lung, head and neck, prostate and colon, ovary and breast, hepatocellular carcinoma. Taking COX-2 inhibitor drugs regularly may reduce the rates of certain cancers and cancer related deaths. Upregulation of COX-2 in tumor tissues has been reported to be accompanied by high levels of $PGE_2$. Moreover, EP2 activation by $PGE_2$ can promote cancer cell growth and invasion by activating iNOS/guanylate cyclase (GC) and mitogen-activated protein kinase (MAPK)-ERK1/2 via PKA-mediated epidermal growth factor (EGF) receptor activation. $PGE_2$/EP2 signaling in mammary epithelial cells triggers hyperplasia of mammary glands and EP2 receptor is an important element for $PGE_2$ regulated vascular endothelial growth factor (VEGF) induction in mouse mammary tumor cells. EP2 signaling directly regulates tumor angiogenesis in endothelium by enhancing endothelial cell motility and cell survival, mediates epidermal hypertrophy and tumor aggression in response to ultraviolet (UV)-irradiation, and induces skin carcinogenesis.

Thus, within certain embodiments, it is contemplated that compounds disclosed herein may be used for the treatment of cancers and tumors of the nervous system including those subjects diagnosed with cancer, including, skin, blood vessel, lung, head and neck, prostate and colon, ovary and breast cancer and hepatocellular carcinoma.

Within certain embodiments, it is contemplated that compounds disclosed herein may be used for the treatment of inflammation generally and autoimmune diseases, such as, but not limited to, encephalomyelitis, leukoencephalitis, Addison's disease, agammaglobulinemia, alopecia areata, amyotrophic lateral sclerosis, ankylosing spondylitis, anti-GBM/TBM nephritis, antiphospholipid syndrome, antisynthetase syndrome, atopic allergy, atopic dermatitis, aplastic anemia, cardiomyopathy, enteropathy, hemolytic anemia, hepatitis, inner ear disease, lymphoproliferative syndrome, peripheral neuropathy, pancreatitis, polyendocrine syndrome, progesterone dermatitis, thrombocytopenic purpura, urticaria, uveitis, Balo disease/Balo, concentric sclerosis, Bechets syndrome, Berger's disease, Bickerstaffs encephalitis, Blau syndrome, Bullous pemphigoid, Castleman's disease, celiac disease, inflammatory demyelinating polyneuropathy, multifocal osteomyelitis, Churg-Strauss syndrome, cicatricial pemphigoid, Cogan syndrome, cold agglutinin disease, complement component 2 deficiency, cranial arteritis CREST syndrome, Crohns Disease, Cushing's Syndrome, cutaneous leukocytoclastic angiitis, Dego's disease, Dercum's disease Suspected, dermatitis herpetiformis, dermatomyositis, diabetes mellitus type 1, diffuse cutaneous systemic sclerosis, Dressler's syndrome, Discoid lupus, erythematosus, eczema, enthesitis-related arthritis, eosinophilic fasciitis, eosinophilic, gastroenteritis, epidermolysis bullosa acquisita, erythema nodosum, cryoglobulinemia, Evan's syndrome, fibrodysplasia ossificans progressiva, fibrosing aveolitis, gastritis, gastrointestinal pemphigoid, giant cell arteritis, glomerulonephritis, Goodpasture's syndrome, Graves' disease, Guillain-Barré syndrome (GBS), Hashimoto's encephalitis, Hashimoto's thyroiditis, haemolytic anaemia, Henoch-Schonlein purpura, herpes gestationis, hypogammaglobulinemia, demyelinating diseases, pulmonary fibrosis, thrombocytopenic purpura, nephropathy, inclusion body myositis, demyelinating polyneuopathy, interstitial cystitis, Kawasaki's Disease, Lambert-Eaton myasthenic syndrome, leukocytoclastic vasculitis, lichen planus, lichen sclerosus, linear IgA disease (LAD), lupoid hepatitis, lupus erythematosus, Majeed syndrome, Ménière's disease, microscopic polyangiitis, Miller-Fisher syndrome, mixed connective tissue disease, morphea, Mucha-Habermann disease, multiple sclerosis, myasthenia gravis, myositis, meuromyelitis optica, neuromyotonia, occular cicatricial pemphigoid, psoclonus myoclonus syndrome, ord thyroiditis, palindromic rheumatism, PANDAS (pediatric autoimmune neuropsychiatric disorders associated with *streptococcus*), paraneoplastic cerebellar degeneration, paroxysmal nocturnal hemoglobinuria (PNH), Parry Romberg syndrome, Parsonnage-Turner syndrome, Pars planitis, pemphigus pernicious anaemia, perivenous encephalomyelitis, POEMS syndrome, polyarteritis *nodosa*, polymyalgia rheumatic, polymyositis, primary biliary cirrhosis, primary sclerosing cholangitis, progressive inflammatory neuropathy, psoriasis Accepted, psoriatic arthritis, pyoderma gangrenosum, pure red cell aplasia, Rasmussen's encephalitis, Raynaud phenomenon, relapsing polychondritis, Reiter's syndrome, Restless leg syndrome, retroperitoneal fibrosis, rheumatoid arthritis, rheumatoid fever, sarcoidosis, Schmidt syndrome, Schnitzler syndrome, scleritis, scleroderma, Sjögren's syndrome, spondyloarthropathy, Still's disease, stiff person syndrome, subacute bacterial endocarditis (SBE), Susac's syndrome, Sweet's syndrome, sydenham chorea, sympathetic ophthalmia, Takayasu's arteritis, temporal arteritis, Tolosa-Hunt syndrome, transverse myelitis, ulcerative colitis, undifferentiated connective tissue disease, undifferentiated spondyloarthropathy, vasculitis, vitiligo, and Wegener's granulomatosis.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound contains a hydrogen-donating heteroatom (e.g. NH), salts are contemplated to covers isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Depending upon the manner of introduction, the compounds described herein may be formulated in a variety of ways. Formulations containing one or more inhibitors can be prepared in various pharmaceutical forms, such as granules, tablets, capsules, suppositories, powders, controlled release formulations, suspensions, emulsions, creams, gels, ointments, salves, lotions, or aerosols and the like. Preferably, these formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, PA: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or non-ionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-beta-alanine, sodium N-lauryl-beta-iminodipropionate, myristo-amphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The concentration of the inhibitor(s) to carrier and/or other substances may vary from about 0.5 to about 100 wt. % (weight percent). For oral use, the pharmaceutical formulation will generally contain from about 5 to about 100% by weight of the active material. For other uses, the pharmaceutical formulation will generally have from about 0.5 to about 50 wt. % of the active material.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Eudragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

The formulation can provide pulsatile delivery of the one or more inhibitors. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

In one embodiment, the compound is formulated for topical administration. Suitable topical dosage forms include lotions, creams, ointments, and gels. A "gel" is a semisolid system containing a dispersion of the active agent, i.e., inhibitor, in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Methods for preparing lotions, creams, ointments, and gels are well known in the art.

The compounds described herein can be administered adjunctively with other active compounds. These compounds include but are not limited to analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics. "Adjunctive administration", as used herein, means the inhibitors can be administered in the same dosage form or in separate dosage forms with one or more other active agents.

Specific examples of compounds that can be adjunctively administered with the compounds include, but are not limited to, aceclofenac, acetaminophen, adomexetine, almotriptan, alprazolam, amantadine, amcinonide, aminocyclopropane, amitriptyline, amolodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproxex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketaserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methylsalicylate, methysergid(e), metoclopramide, mianserin, mifepristone, milnacipran, minaprine, mirtazapine, moclobemide, modafinil (an anti-narcoleptic), molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprazin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propanolol, propizepine, propoxyphene, protriptyline, quazepam, quinupramine, reboxitine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenozine, thiazides, thioridazine, thiothixene, tiapride, tiasipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

The additional active agent(s) can be formulated for immediate release, controlled release, or combinations thereof.

EXPERIMENTAL
Inodole Amide Derivatives as EP2 Antagonists
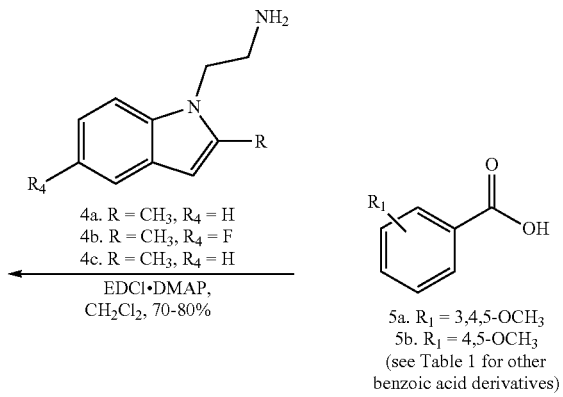
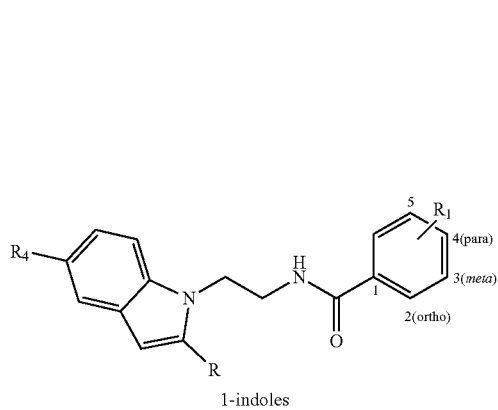
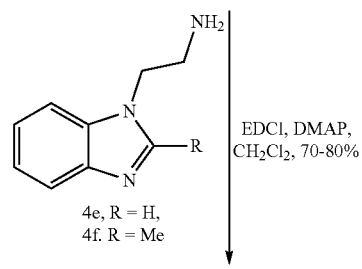
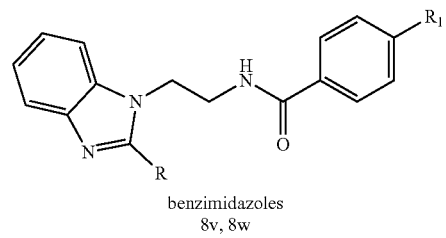
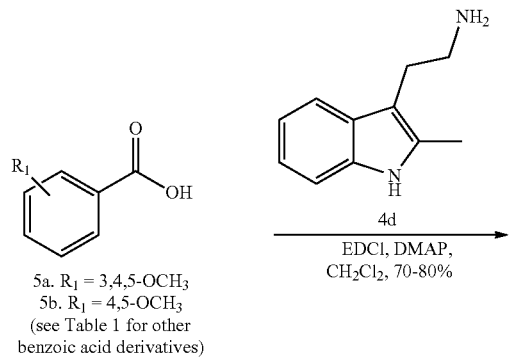
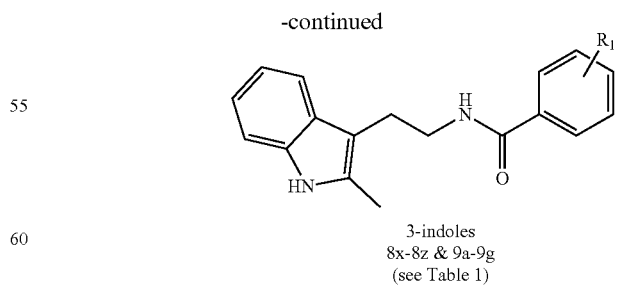
Amide derivatives 6a and 6b were synthesized as starting from 2-(2-methyl-H-indol-1-yl)ethan-1-amine (4a) and 3,4,5-trimethoxybenzoic acid (5a) and 3,4-dimethoxy benzoic acid (5b). The other substituted derivatives on the phenyl ring (6c-z, 7a-z, & 8a-u), isomeric 3-inodole derivatives ((8x-z, & 9a-g), and imidazole derivatives ((8v-w) were synthesized analogous to 6a and 6b as illustrated.

Table 1 provided data for individual structures. Schild $K_B$ values are calculated using the formula $\log(dr-1) = \log X_B - \log K_B$, where dr (dose ratio) = fold shift in $EC_{50}$ of $PGE_2$ by the test compound, $X_B$ is antagonist concentration [1 μM]. $K_B$ value indicates a concentration required to produce a 2-fold rightward shift of PGE2 concentration response curve. KB values are average of 2-3 measurements run in duplicate.

TABLE 1

Structures and bioactivity of EP2 antagonists $RCH_2CH_2NH(C=O)R^1$

| Entry | Compd. ID | R | $R_1$ | EP2 $K_B$ (nM) |
|---|---|---|---|---|
| 6a | TG7-112-1 | 2-methylindol-1-yl | 3,4,5-trimethoxyphenyl | >1000 |
| 6b | TG7-112-2 | 2-methylindol-1-yl | 3,4-dimethoxyphenyl | 22.3 |
| 6c | TG7-224 | 2-methylindol-1-yl | 4-methoxyphenyl | 75.6 |
| 6d | TG7-237 | 2-methylindol-1-yl | 4-(ethylamino)phenyl | 15.5 |
| 6e | TG7-142 | 2-methylindol-1-yl | 4-(dimethylamino)phenyl | 9.8 |
| 6f | TG7-171 | 2-methylindol-1-yl | 4-(diethylamino)phenyl | 2.7 |
| 6g | TG7-192 | 2-methylindol-1-yl | 4-(dipropylamino)phenyl | 11.9 |

TABLE 1-continued

Structures and bioactivity of EP2 antagonists RCH$_2$CH$_2$NH(C=O)R$^1$

| Entry | Compd. ID | R | R$_1$ | EP2 K$_B$ (nM) |
|---|---|---|---|---|
| 6h | TG7-188 | 2-methylindol-1-yl | 4-(N,N-dibutylamino)phenyl | 68.8 |
| 6i | TG7-143 | 2-methylindol-1-yl | 4-aminophenyl | 210 |
| 6j | TG7-223 | 2-methylindol-1-yl | 4-hydroxyphenyl | >1000 |
| 6k | TG7-179 | 2-methylindol-1-yl | 4-guanidinophenyl | >1000 |
| 6l | TG7-205 | indol-1-yl | 4-(N,N-diethylamino)phenyl | 62.9 |
| 6m | TG7-233 | 2-methylindol-1-yl | 4-acetoxyphenyl | 150 |
| 6n | TG7-117 | 2-methylindol-1-yl | 4-acetamidophenyl | 97 |
| 6o | TG7-157 | 2-methylindol-1-yl | 4-(2-fluorobenzamido)phenyl | 51 |

TABLE 1-continued

Structures and bioactivity of EP2 antagonists RCH$_2$CH$_2$NH(C=O)R$^1$

| Entry | Compd. ID | R | R$_1$ | EP2 K$_B$ (nM) |
|---|---|---|---|---|
| 6p | TG7-140 | 2-methylindol-1-yl | 4-(C(O)NH$_2$)-phenyl | 150 |
| 6q | TG7-227 | 2-methylindol-1-yl | 4-(C(O)N(CH$_3$)$_2$)-phenyl | >1000 |
| 6r | TG7-226 | 2-methylindol-1-yl | 4-(C(O)N(Et)$_2$)-phenyl | 800 |
| 6s | TG7-147 | 2-methylindol-1-yl | 4-CN-phenyl | 140 |
| 6t | TG7-172 | 2-methylindol-1-yl | 4-COO$^t$Bu-phenyl | 100 |
| 6u | TG7-176 | 2-methylindol-1-yl | 4-COOH-phenyl | 245 |
| 6v | TG7-161 | 2-methylindol-1-yl | 4-SO$_2$NH$_3$-phenyl | 486 |
| 6w | TG7-165 | 2-methylindol-1-yl | 3-SO$_2$NH$_3$-phenyl | >1000 |
| 6x | TG7-254 | 2-methylindol-1-yl | 4-(CH$_2$NHBoc)-phenyl | 84 |

TABLE 1-continued
Structures and bioactivity of EP2 antagonists RCH$_2$CH$_2$NH(C=O)R$^1$
| Entry | Compd. ID | R | R$_1$ | EP2 K$_B$ (nM) |
|---|---|---|---|---|
| 6y | TG7-258 | 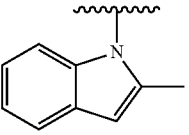 [SMILES: *n1c(C)cc2ccccc21] | 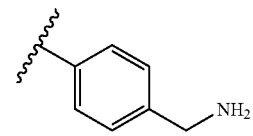 [SMILES: *c1ccc(CN)cc1] | 690 |
| 6z | TG7-272 | 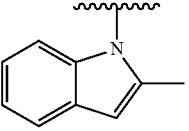 [SMILES: *n1c(C)cc2ccccc21] | 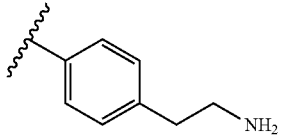 | 1220 |
| 7a | TG7-164 | 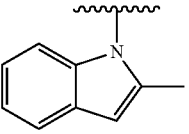 [SMILES: *n1c(C)cc2ccccc21] | 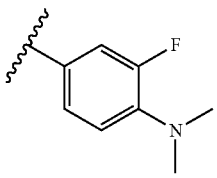 [SMILES: *c1ccc(N(C)C)c(F)c1] | 18.1 |
| 7b | TG7-158 | 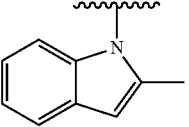 [SMILES: *n1c(C)cc2ccccc21] | 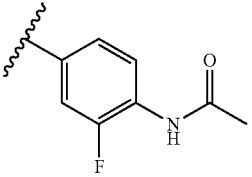 [SMILES: *c1ccc(NC(C)=O)c(F)c1] | 530 |
| 7c | TG7-225 | 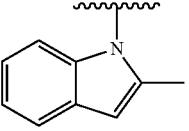 [SMILES: *n1c(C)cc2ccccc21] | 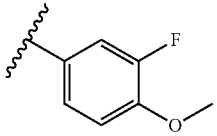 [SMILES: *c1ccc(OC)c(F)c1] | 86.8 |
| 7d | TG7-206 | 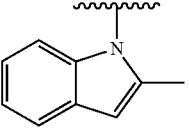 [SMILES: *n1c(C)cc2ccccc21] | 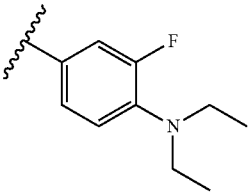 [SMILES: *c1ccc(N(CC)CC)c(F)c1] | 4.6 |
| 7e | TG7-213 | 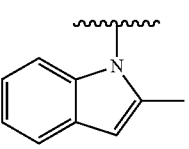 [SMILES: *n1c(C)cc2ccccc21] | 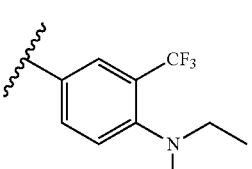 | 310 |
| 7f | TG6-201 | 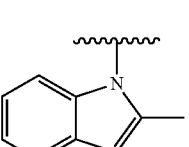 | 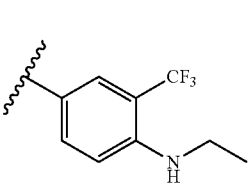 [SMILES: *c1ccc(NCC)c(C(F)(F)F)c1] | 20.2 |

TABLE 1-continued

Structures and bioactivity of EP2 antagonists RCH$_2$CH$_2$NH(C=O)R$^1$

| Entry | Compd. ID | R | R$_1$ | EP2 K$_B$ (nM) |
|---|---|---|---|---|
| 7g | TG7-214 | 2-methylindol-1-yl | 3-methoxy-4-(diethylamino)phenyl | 61.2 |
| 7h | TG7-155-1 | 2-methylindol-1-yl | 3-fluoro-4-cyanophenyl | 140 |
| 7i | TG7-155-2 | 2-methylindol-1-yl | 3-fluoro-4-cyanophenyl (isomer) | 280 |
| 7j | TG7-173 | 2-methylindol-1-yl | 4-(pyrrolidin-1-yl)phenyl | 24.7 |
| 7k | TG7-152 | 2-methylindol-1-yl | 4-(piperidin-1-yl)phenyl | 9.4 |
| 7l | TG7-240 | 2-methylindol-1-yl | 4-(4-methylpiperidin-1-yl)phenyl | 30.3 |
| 7m | TG8-24 | 2-methylindol-1-yl | 4-(4-(ethoxycarbonyl)piperidin-1-yl)phenyl | 500 |

TABLE 1-continued
Structures and bioactivity of EP2 antagonists RCH$_2$CH$_2$NH(C=O)R$^1$
| Entry | Compd. ID | R | R$_1$ | EP2 K$_B$ (nM) |
|---|---|---|---|---|
| 7n | TG8-29 | 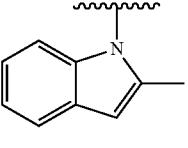 [SMILES: *n1c(C)cc2ccccc21] | 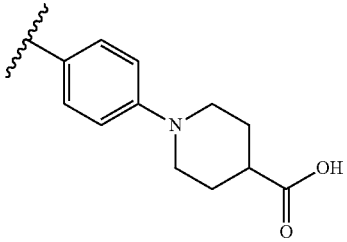 [SMILES: *c1ccc(N2CCC(C(=O)O)CC2)cc1] | 89.7 |
| 7o | TG7-185 | 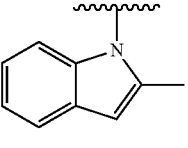 [SMILES: *n1c(C)cc2ccccc21] | 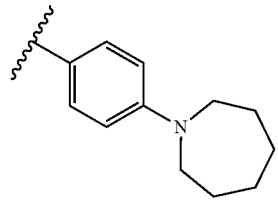 [SMILES: *c1ccc(N2CCCCCC2)cc1] | 22.6 |
| 7p | TG7-170 | 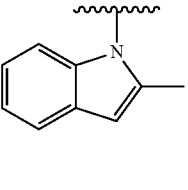 [SMILES: *n1c(C)cc2ccccc21] | 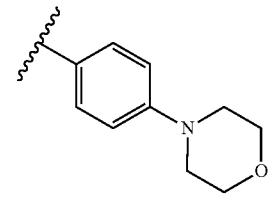 [SMILES: *c1ccc(N2CCOCC2)cc1] | 9.6 |
| 7q | TG7-166 | 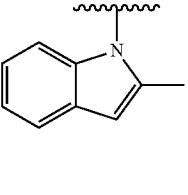 [SMILES: *n1c(C)cc2ccccc21] | 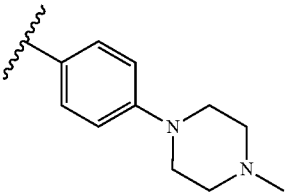 [SMILES: *c1ccc(N2CCN(C)CC2)cc1] | 64 |
| 7r | TG7-255 | 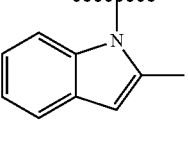 | 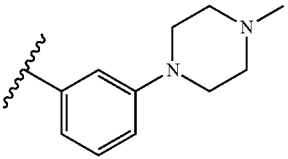 [SMILES: *c1cccc(N2CCN(C)CC2)c1] | 770 |
| 7s | TG7-256 | 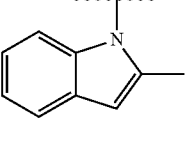 | 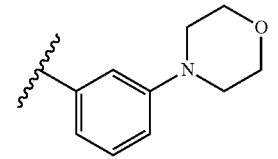 [SMILES: *c1cccc(N2CCOCC2)c1] | >1000 |
| 7t | TG7-153 | 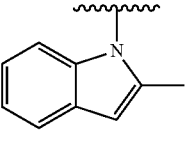 [SMILES: *n1c(C)cc2ccccc21] | 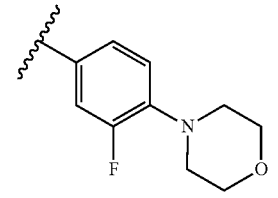 [SMILES: *c1ccc(N2CCOCC2)c(F)c1] | 25.7 |

TABLE 1-continued

Structures and bioactivity of EP2 antagonists RCH$_2$CH$_2$NH(C=O)R$^1$

| Entry | Compd. ID | R | R$_1$ | EP2 K$_B$ (nM) |
|---|---|---|---|---|
| 7u | TG7-141 | 2-methylindol-1-yl | 4-(4-methylpiperazin-1-yl)-3-fluorophenyl | 45 |
| 7v | TG7-182 | 2-methylindol-1-yl | 4-(4-methyl-1,4-diazepan-1-yl)phenyl | 148 |
| 7w | TG7-180 | 2-methylindol-1-yl | 4-(4-hydroxypiperidin-1-yl)phenyl | 26.8 |
| 7x | TG7-159 | 2-methylindol-1-yl | 4-(1H-tetrazol-1-yl)phenyl | 42.2 |
| 7y | TG8-8 | 2-methylindol-1-yl | 4-(5-thioxo-4,5-dihydro-1H-tetrazol-1-yl)phenyl | 32.2 |
| 7z | TG8-15 | 2-methylindol-1-yl | 4-(1H-tetrazol-5-yl)phenyl | 22.3 |
| 8a | TG7-178 | 2-methylindol-1-yl | 1,3-dimethyl-2-oxo-2,3-dihydro-1H-benzo[d]imidazol-5-yl | 20.9 |

TABLE 1-continued

Structures and bioactivity of EP2 antagonists RCH$_2$CH$_2$NH(C=O)R$^1$

| Entry | Compd. ID | R | R$_1$ | EP2 K$_B$ (nM) |
|---|---|---|---|---|
| 8b | TG7-193 | 2-methylindol-1-yl | 4-cyclohexylphenyl | 120 |
| 8c | TG7-202-2 | 2-methylindol-1-yl | 4-(piperazin-1-yl)phenyl | 410 |
| 8d | TG7-211 | 2-methylindol-1-yl | 4-(4-acetylpiperazin-1-yl)phenyl | 50.2 |
| 8e | TG7-257 | 2-methylindol-1-yl | 1H-benzotriazol-5-yl | 87.5 |
| 8f | TG7-207 | 2-methylindol-1-yl | 2-thioxo-4-oxo-1,2,3,4-tetrahydroquinazolin-6-yl | 84.1 |
| 8g | TG7-264 | 2-methylindol-1-yl | 4-(1-Boc-piperidin-3-yl)phenyl | 95 |
| 8h | TG7-268 | 2-methylindol-1-yl | 4-(piperidin-3-yl)phenyl | >1000 |

TABLE 1-continued

Structures and bioactivity of EP2 antagonists RCH$_2$CH$_2$NH(C=O)R$^1$

| Entry | Compd. ID | R | R$_1$ | EP2 K$_B$ (nM) |
|---|---|---|---|---|
| 8i | TG7-234 | 2-methylindol-1-yl | 4-(piperidin-4-yloxy)phenyl | >1000 |
| 8j | TG8-5 | 2-methylindol-1-yl | 4-(morpholinomethyl)phenyl | 970 |
| 8k | TG8-5 | 2-methylindol-1-yl | 4-((4-methylpiperazin-1-yl)methyl)phenyl | >1000 |
| 8l | TG7-261 | 2-methylindol-1-yl | 2-aminopyrimidin-5-yl | >1000 |
| 8m | TG7-228 | 2-methylindol-1-yl | 2-(phenylamino)pyrimidin-5-yl | 1.6 |
| 8n | TG7-229 | 2-methylindol-1-yl | 2-(ethylamino)pyrimidin-5-yl | 57.8 |
| 8o | TG7-249 | 2-methylindol-1-yl | 2-morpholinopyrimidin-5-yl | 76.5 |
| 8p | TG7-259 | 2-methylindol-1-yl | 2-aminopyridin-3-yl | 520 |
| 8q | TG7-244 | 2-methylindol-1-yl | 4-(pyrimidin-2-yl)cyclohexyl | 380 |

TABLE 1-continued
Structures and bioactivity of EP2 antagonists RCH$_2$CH$_2$NH(C=O)R$^1$
| Entry | Compd. ID | R | R$_1$ | EP2 K$_B$ (nM) |
|---|---|---|---|---|
| 8r | TG7-183 | 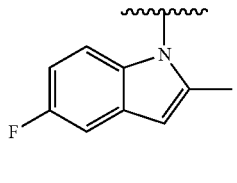 [SMILES: *n1c(C)cc2cc(F)ccc21] | 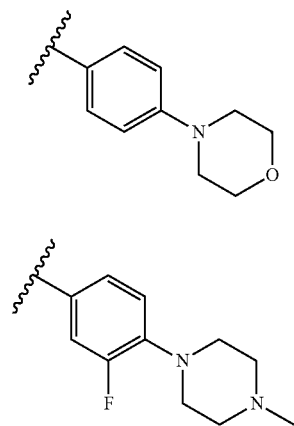 | 14.9 |
| 8s | TG7-184 | 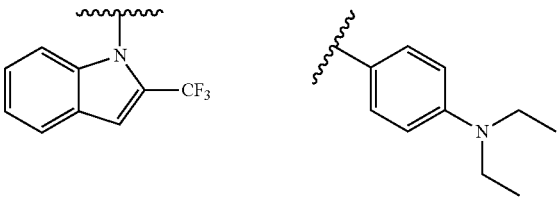 | 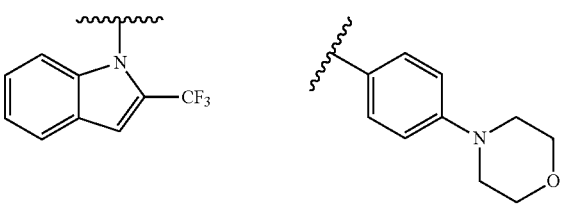 | 62.2 |
| 8t | TG7-194 | 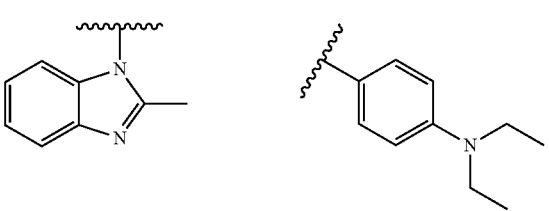 | 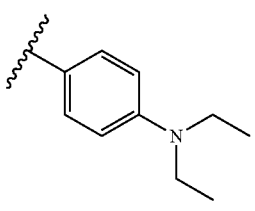 [SMILES: *c1ccc(N(CC)CC)cc1] | 150 |
| 8u | TG7-195 | 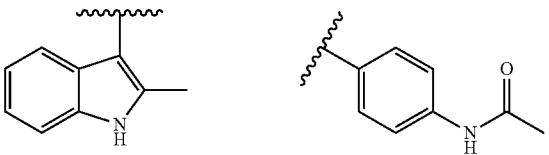 | | 120 |
| 8v | TG7-199 | | | 190 |
| 8w | TG7-203 | | | >1000 |
| 8x | TG7-146 | | | 138 |

TABLE 1-continued
Structures and bioactivity of EP2 antagonists RCH$_2$CH$_2$NH(C=O)R$^1$
| Entry | Compd. ID | R | R$_1$ | EP2 K$_B$ (nM) |
|---|---|---|---|---|
| 8y | TG7-231 | 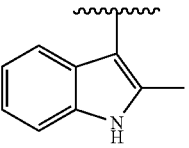 [SMILES: *c1c(C)[nH]c2ccccc12] | 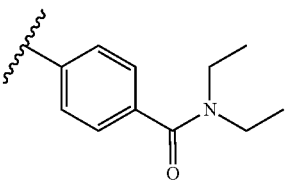 [SMILES: *c1ccc(C(=O)N(CC)CC)cc1] | >1000 |
| 8z | TG7-167 | 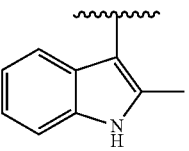 [SMILES: *c1c(C)[nH]c2ccccc12] | 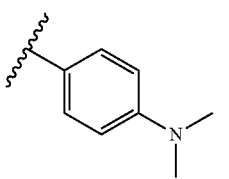 [SMILES: *c1ccc(N(C)C)cc1] | 10.8 |
| 9a | TG7-181 | 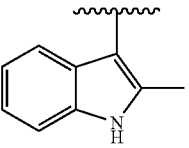 [SMILES: *c1c(C)[nH]c2ccccc12] | 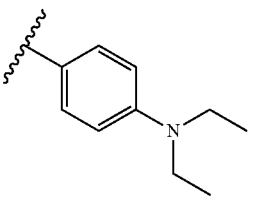 [SMILES: *c1ccc(N(CC)CC)cc1] | 6.9 |
| 9b | TG7-168 | 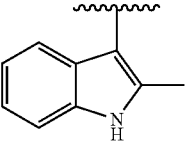 [SMILES: *c1c(C)[nH]c2ccccc12] | 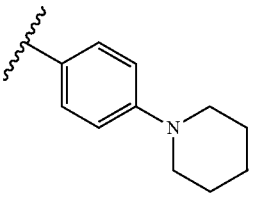 [SMILES: *c1ccc(N2CCCCC2)cc1] | 19.8 |
| 9c | TG7-174 | 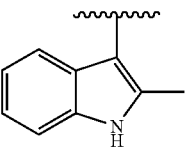 [SMILES: *c1c(C)[nH]c2ccccc12] | 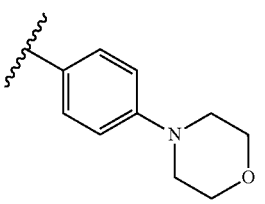 [SMILES: *c1ccc(N2CCOCC2)cc1] | 28.6 |
| 9d | TG7-175 | 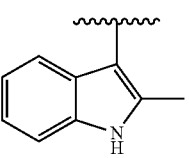 [SMILES: *c1c(C)[nH]c2ccccc12] | 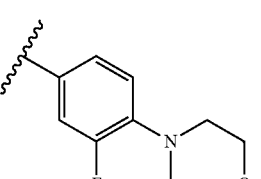 | 66 |
| 9e | TG7-169 | 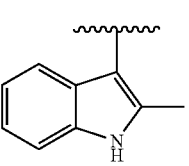 [SMILES: *c1c(C)[nH]c2ccccc12] | 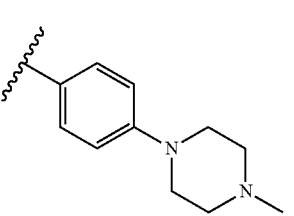 [SMILES: *c1ccc(N2CCN(C)CC2)cc1] | 135 |

TABLE 1-continued

Structures and bioactivity of EP2 antagonists RCH$_2$CH$_2$NH(C=O)R$^1$

| Entry | Compd. ID | R | R$_1$ | EP2 K$_B$ (nM) |
|---|---|---|---|---|
| 9f | TG7-232 | 2-methyl-1H-indol-3-yl | 2-(ethylamino)pyrimidin-5-yl | 155 |
| 9g | TG8-9 | 2-methyl-1H-indol-3-yl | 2-morpholinopyrimidin-5-yl | 280 |
| 9h | TG7-118 | 2-methyl-1H-indol-1-yl | 5-fluoro-1H-benzimidazol-2-yl | 130 |
| 9i | TG7-148 | 2-methyl-1H-indol-1-yl | 6-fluoro-4-hydroxyquinolin-3-yl | 175 |
| 9j | TG7-120 | 2-methyl-1H-indol-1-yl | 5-oxopyrrolidin-2-yl | >1000 |

The 3,4,5-trimethoxyamide derivative 6a showed no EP2 activity, where as the 4,5-dimethoxyamide derivative 6b displayed strong EP2 potency (Schild K$_B$=22 nM).

A para-dimethylaminoamide (6e), or para diethylaminoamide (6f) exhibited about 2-fold or 8-fold improved EP2 potency respectively in comparison to 6b. The dipropylamino derivative displayed 2-fold higher potency than 6b. A tert-butylcarboxylate protected para-methylamino derivative (6x) showed 2.4-fold higher potency than the free para-amino derivative (6i) (Table 1).

A variety of nitrogen heterocyclic rings at the para-position of the phenyl ring were synthesized and examined. Pyrrolidine (7j) and homopiperidine (7o) derivatives showed potency. A piperidine derivative (7k) and a morpholine derivative (7p) both displayed about 2.3-fold higher EP2 potency than 6b, (Table 2). The 5-tetrazole (7z) and the benzofused-imidazole (8a) displayed potency. A 2-phenylamino derivative of 2-aminopyrimidine-amide (8m) exhibited a EP2 potency (Schild KB=1.6 nM). A 2-ethylamino derivative (8n) or, 2-morpholino derivative (8o) showed EP2 potency of 58 and 76.5 nM, respectively.

TABLE 2

EP2 potency, selectivity and cytotoxicity of EP2 antagonists

| Entry (Compd. ID) | K$_B$ EP2 nM | K$_B$ EP4 μM | Selective Index EP4/EP2 | K$_B$ DP1 nM | Selective Index (DP1/EP2) | K$_B$ IP μM | Selective Index (IP/EP2) | CC$_{50}$ (μM) | Therapeutic Index (CC$_{50}$/EP2 K$_B$) |
|---|---|---|---|---|---|---|---|---|---|
| 6e TG7-142 | 9.8 | 51 | 5,230 | 6430 | 655 | 4.7 | 480 | 310 | 31,630 |
| 6f TG7-171 | 2.7 | 31.3 | 11,590 | 3190 | 1,220 | 8.0 | 2,960 | 320 | 118,520 |
| 6g TG7-192 | 11.8 | 15.5 | 1320 | 3550 | 298 | 1.12 | 95 | 332 | 28,130 |
| 7j TG7-173 | 24.7 | 28.7 | 1,160 | >10000 | >516 | 14.2 | 570 | 337 | 16,120 |
| 7k TG7-152 | 9.4 | 30.2 | 3,210 | 2570 | 273 | 3.4 | 360 | 315 | 33,510 |

TABLE 2-continued

EP2 potency, selectivity and cytotoxicity of EP2 antagonists

| Entry (Compd. ID) | $K_B$ EP2 nM | $K_B$ EP4 μM | Selective Index EP4/EP2 | $K_B$ DP1 nM | Selective Index (DP1/EP2) | $K_B$ IP μM | Selective Index (IP/EP2) | $CC_{50}$ (μM) | Therapeutic Index ($CC_{50}$/EP2 $K_B$) |
|---|---|---|---|---|---|---|---|---|---|
| 7o TG7-185 | 22.6 | 23.6 | 1,045 | 7720 | 342 | 8.5 | 375 | 327 | 14,470 |
| 7p TG7-170 | 9.6 | 21 | 2,190 | 5210 | 533 | 1.98 | 206 | 289 | 30,100 |
| 7t TG7-153 | 25.7 | 14.5 | 565 | 2200 | 85 | 5.6 | 217 | >500 | >19,450 |
| 7u TG7-141 | 45 | 4.76 | 106 | 980 | 22 | 64.0 | 1,420 | 300 | 6,660 |
| 7w TG7-180 | 26.8 | 70.3 | 2,629 | 4620 | 172 | 18.1 | 675 | 163 | 6,082 |
| 7z TG8-15 | 22.3 | >10000 | 584 | 660 | 29 | >10000 | 1040 | >300 | >13,450 |
| 8a TG7-178 | 20.9 | 36.1 | 1730 | 6290 | 300 | 25.2 | 1200 | 154 | 7,370 |
| 8z TG7-167 | 10.8 | 16.4 | 1,520 | 3610 | 334 | 63.1 | 5,840 | 320 | 29,630 |
| 9a TG7-181 | 6.9 | 48 | 6,945 | 9480 | 1374 | >10000 | ND | >500 | >72,460 |
| 9c TG7-174 | 28.6 | 75.6 | 2,645 | 7790 | 272 | 85.0 | 2,970 | 311 | 10,870 |

EP2, EP4, DP1 and IP KBS are average of 2-3 independent experiments run in duplicate. $CC_{50}$ are average one measurement run in triplicate. $CC_{50}$=critical concentration required to kill 50% cells.

The 3-indole isomeric derivatives showed nearly similar potency to their 1-indole equivalent compounds (cf. 8x vs.6n; 8y vs. 6r; 8z vs. 6e; 9a vs. 6f; 9b vs.7k; 9c vs.7p; 9d vs. 7t; 9e vs.7q), indicating both 1-indole and 3-indole derivatives are, in general, are potent antagonist of EP2 receptor. The compounds 6f, 7p, 7z, 8z, 9a and 7k, 7p display high EP2 potency, with Schild KB approximately 10 nM.

Selectivity Against Other Prostanoid Receptors

The EP2 receptor is a member of the prostanoid receptor family and shares 20-30% structural homology with EP1, EP3 and EP4, all which are activated by a common agonist PGE2. However, EP2 exhibits the highest amino acid homology to DP1 (44%) and IP (40%) receptors, which are activated by PGD2 and PGI2 respectively. Furthermore, studies indicate that DP1 has similar physiological functions as EP2, whereas the activation of the IP receptor is shown to be important for cardioprotection. EP2, EP4, DP1 and IP are all Gas-coupled transmembrane receptor. The selectivity of the novel EP2 antagonists was examined over EP4, DP1 and IP.

For example, 6f displayed >1200-fold selectivity against DP1 receptor (Table 2), compound 6e displayed 655-fold, and 7j and 7p showed 516-fold and 533-fold selectivity over DP1 respectively. Moreover, compounds 6g, 7k, and 10z displayed over 275-fold selectivity against DP1.

Several of compounds were examined against EP4 and IP receptors at single concentration of 10 μM. The extrapolated Schild KBS for these receptors are shown Table 2. A vast majority of these derivatives displayed >1000-fold selectivity over EP4, but a few derivatives such as 7t, and 7z displayed only ~600-fold selectivity, and one other compound 7u displayed a moderate (100-fold) selectivity. Several of these compounds also displayed selectivity against the IP receptor. For example 6f and 9c displayed ~3000-fold selectivity; 7z, and 8a exhibited >1000-fold selectivity; 7j, 7k, and 7w exhibited selectivity in the range of 300 to 600-fold. Furthermore, these derivatives were tested to determine whether they reduced viability of the parent C6-glioma cells, but a majority of these derivatives showed an effect only at high micromolar concentrations (>300 μM) with in vitro therapeutic indexes >10000, except two compounds 7w and 8a, both of which showed an effect on cell viability at >100 uM. Nonetheless, in vitro therapeutic indexes >6000-fold indicating that the bioactivity by this class of amide compounds is not driven by cell viability (Table 2).

Competitive Mechanism of Inhibition

Figure 3:
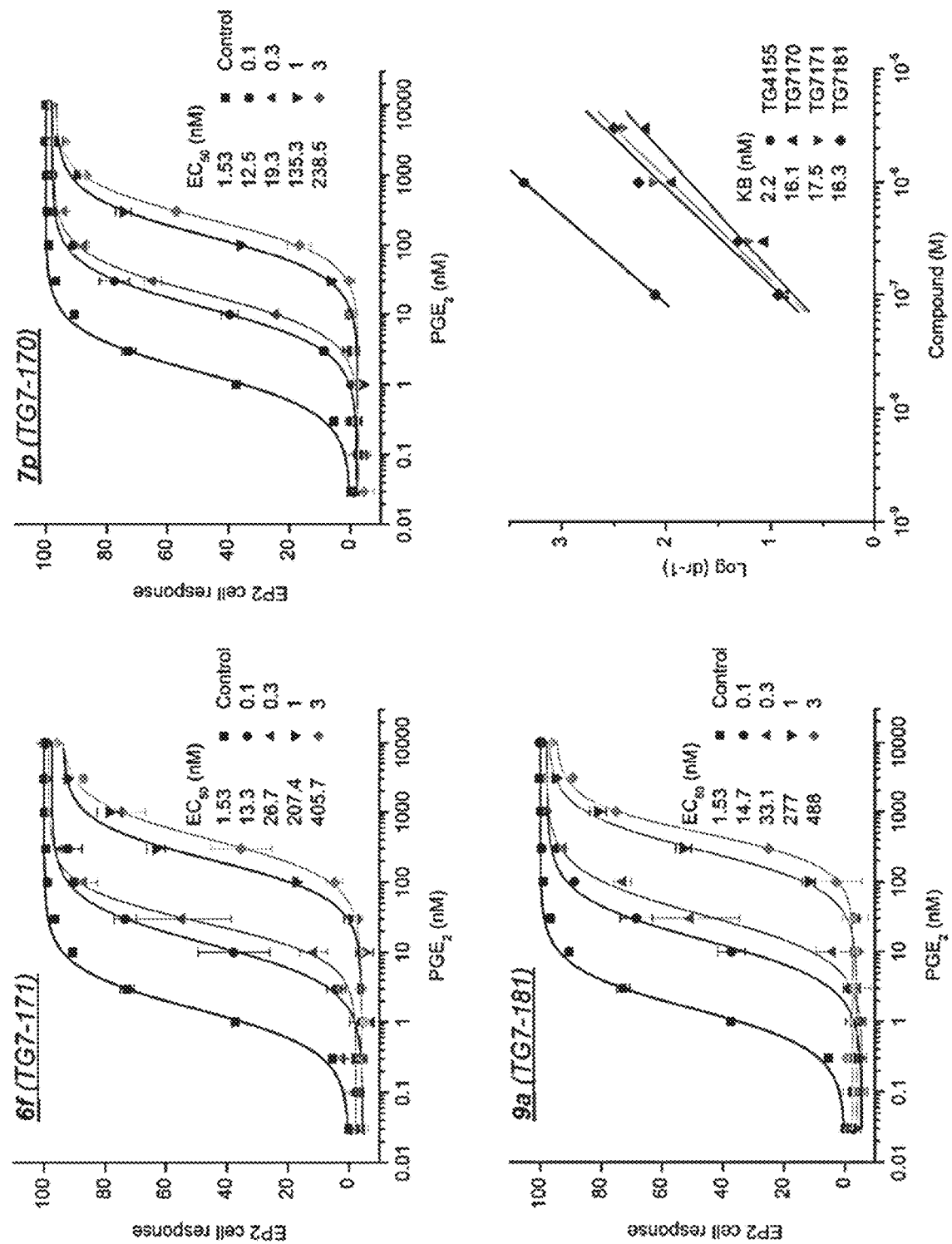
FIG. 3 shows data indicating competitive antagonism of EP2 receptor by the amide analogs. Compounds 6f, 7p, and 9a inhibits PGE2-induced human EP2 receptor activation in a concentration dependent manner. Schild regression analysis is performed to determine the modality of antagonism by these compounds. $K_B$ values from this experiment are slightly different from the values shown Table-1 which are derived from a single concentration test. The Schild plot and the $K_B$ value of N-(2-(2-methyl-1H-indol-1-yl)ethyl)-3-(3, 4,5-trimethoxyphenyl)acrylamide compound 1 is shown.

Compounds 6f, 7p, 9a were evaluated for mechanism of inhibition by subjected them to a concentration-response test on EC50 of PGE2 on EP2 receptors overexpressed in C6-glioma cells. A linear regression of log (dr-1) on log $X_B$ with slope of unity characterizes a competitive antagonism. Schild $K_B$ values are derived by the equation log (dr−1)=log $X_B$−log $K_B$, where dr=dose ratio, i.e. the fold shift in $EC_{50}$; $X_B$ is [antagonist], and $K_B$ is the equilibrium dissociation constant for the antagonist-receptor complex. $K_B$ value indicates the antagonist concentration required for a twofold rightward shift in the PGE2 dose-response curve. Thus, a lower $K_B$ value indicates a higher inhibitory potency. The selected members of the second generation compounds induced a concentration-dependent, parallel, rightward shift in the PGE2 concentration-response curve (FIG. 3). The Schild regression analyses indicate that these compounds have a competitive mechanism of antagonism of EP2 (FIG. 3). Moreover, a less potent carboxylic acid derivative (7n), and a 5-tetrazole derivative (7z) also indicated competitive antagonism of EP2 with Schild KB 97 nM for 7n, and 16.4 nM for 7z.

Liver Microsomal Stability and Pharmacokinetics

Compounds 7j, 7k, 7x, & 8m displayed >7% remaining at 60 minutes in mouse liver fractions. A 5-tetrazole derivative 7z and a carboxypiperidine derivative 7n, both of which displayed high stability in mouse and human liver microsomes with greater than 50% remaining at 60 min. These two derivatives also displayed high aqueous solubility by nephelometry, when measured in PBS buffer (pH 7.4) with 1% DMSO. Compound 7z was selected it for in vivo pharmacokinetic study. It displayed about 12-fold higher peak concentrations in plasma by intraperitoneal (ip) route of administration, in comparison to an oral route (po). It displayed plasma half-life (t1/2) about 0.3 hrs by ip route.

N-(2-(2-Methyl-1H-indol-1-yl)ethyl)-4-(piperidin-1-yl)benzamide (7k) (TG7-152)

(Typical procedure): A solution of 2-(2-methyl-1H-indol-1-yl)ethanamine (4a) (65 mg, 0.373 mmol) and 4-(piperidin-1-yl)benzoic acid (5) (76 mg, 1 eq.), and dimethylaminopyridine (catalytic, ~5 mg) in dichloromethane (6 mL) was added 1-ethyl-3-(3-dimethylaminopropyl)-carbodiimide.hydrochloride (EDCI) (92 mg, 1.3 eq.) at room temperature. The resulting reaction mixture was stirred for 6 h. At the conclusion of the reaction (TLC), water (15 mL) was added to quench the reaction. The product was extracted with ethyl acetate (20 mL×3). Organics were washed with dilute HCl (10 mL), saturated $NaHCO_3$ solution (10 ml), water (10 ml) and brine solution (10 ml) and dried over $Na_2SO_4$ and concentrated. The resulting crude product was subjected to silica gel chromatography eluting with 0-40% ethyl acetate in hexane to furnish 7k (TG7-152) (100 mg, 74% yield). $^1$H NMR (CDCl3): δ 7.52 (d, J=5.6 Hz, 1H), 7.49 (d, J=8.8 Hz, 2H), 7.30 (d, J=8 Hz, 1H), 7.07 (m, 2H), 6.80 (m, 2H), 6.23 (s, 1H), 5.98 (t, J=5.4 Hz, 1H), 4.33 (t, J=6 Hz, 2H), 3.76 (q, J=6 Hz, 2H), 3.25 (t, J=4.8 Hz, 4H), 2.37 (s, 3H), 1.6 (m, 6H). LCMS (ESI): >97% purity at k 254, MS; m/z, 362 [M+H]+. Anal. Calcd. for $C_{23}H_{27}N_3O$: C, 76.42; H, 7.53; N, 11.62. found; C, 75.55; H, 7.50; N, 11.26.

Other compounds were synthesized analogously by this typical procedure in a 70-80% yield, and then characterized by $^1$H NMR and LCMS. Elemental analysis is recorded for selected compounds.

4-(Dimethylamino)-N-(2-(2-methyl-1H-indol-1-yl)ethyl)benzamide (6e) (TG7-142)

$^1$H NMR (CDCl3): δ 7.52 (m, 3H), 7.32 (d, J=7.2, Hz, 1H), 7.08 (m, 2H), 6.63 (d, J=8.8 Hz, 2H), 6.23 (s, 1H), 5.9 (NH, 1H), 4.33 (t, J=5.6 Hz, 2H), 3.76 (q, J=6 Hz, 2H), 2.99 (s, 6H), 2.37 (s, 3H). LCMS (ESI): >97% purity at λ 254, MS; m/z, 395 [M+H]+. Anal. Calcd. for $C_{20}H_{23}N_3O$; C, 74.74; H, 7.21; N, 13.07. Found; C, 74.37; H, 7.16; N, 12.83.

4-(Diethylamino)-N-(2-(2-methyl-1H-indol-1-yl)ethyl)benzamide (6f) (TG7-171)

$^1$H NMR (CDCl3): δ 7.49 (m, 3H), 7.32 (d, J=8 Hz, 1H), 7.08 (m, 2H), 6.56 (d, J=9.2 Hz, 2H), 6.23 (s, 1H), 5.95 (t, J=6 Hz, 1H), 4.32 (t, J=5.6 Hz, 2H), 3.76 (q, J=6 Hz, 2H), 3.37 (q, J=7.2 Hz, 4H), 2.37 (s, 3H), 1.15 (t, J=7.2 Hz, 6H). LCMS (ESI): >97% purity at λ 254, MS; m/z, 350 [M+H]+. Anal. Calcd. for C20H23N3O; C, 75.61; H, 7.79; N, 12.02. Found; C, 75.47; H, 7.74; N, 11.86.

N-(2-(2-Methyl-1H-indol-1-yl)ethyl)-4-(pyrrolidin-1-yl)benzamide (7j) (TG7-173)

$^1$H NMR (CDCl3): δ 7.50 (dd, J=6.8, 2 Hz, 3H), 7.32 (d, J=8.4 Hz, 1H), 7.0 (m, 2H), 6.45 (d, J=8.4 Hz, 2H), 6.23 (s, 1H), 5.96 (t, J=6 Hz, 1H), 4.33 (t, J=6 Hz, 2H), 3.75 (q, J=6 Hz, 2H), 3.29 (t, J=6.4 Hz, 4H), 2.37 (s, 3H), 2.0 (m, 4H). LCMS (ESI): >97% purity at k 254, MS; m/z, 348 [M+H]+. Anal. Calcd. for C22H25N3O; C, 76.05; H, 7.25; N, 12.09. found; C, 75.98; H, 7.25; N, 11.95.

N-(2-(2-Methyl-1H-indol-1-yl)ethyl)-4-morpholino-benzamide (7p) (TG7-170)

$^1$H NMR (CDCl3): δ 7.52 (m, 3H), 7.31 (d, J=8 Hz, 1H), 7.09 (m, 2H), 6.81 (d, J=8.8 Hz, 2H), 6.24 (s, 1H), 5.99 (t, J=6.4 Hz, 1H), 4.34 (t, J=5.6 Hz, 2H), 3.83 (t, J=4.8 Hz, 4H), 3.77 (q, J=5.6 Hz, 2H), 3.21 (t, J=5.2 Hz, 4H), 2.37 (s, 3H). LCMS (ESI): >97% purity at λ 254, MS; m/z, 364 [M+H]+. Anal. Calcd for C22H25N3O2; C, 72.70; H, 6.93; N, 11.56. found, C, 72.49; H, 6.91; N, 11.39

1,3-Dimethyl-N-(2-(2-methyl-1H-indol-1-yl)ethyl)-2-oxo-2,3-dihydro-1H-benzo[d]imidazole-5-carboxamide (8a) (TG7-178)

$^1$H NMR (CDCl3): δ 7.53 (dd, J=6.4, 1.6 Hz, 1H), 7.32 (d, J=8 Hz, 1H), 7.27 (s, 1H), 7.25 (m, 1H), 7.0 (m, 2H), 6.88 (d, J=8 Hz, 1H), 6.28 (s, 1H), 6.10 (t, J=5.6 Hz, 1H), 4.37 (t, J=6 Hz, 2H), 3.8 (q, J=5.6 Hz, 2H), 3.40 (s, 3H), 2.39 (s, 3H). LCMS (ESI): >95% purity at λ 254, MS; m/z, 363 [M+H]+. Anal. Calcd. for C21H22N4O2; C, 69.59; H, 6.12; N, 15.46. found; C, 69.45; H, 6.14; N, 15.36.

4-(Diethylamino)-N-(2-(2-methyl-1H-indol-3-yl)ethyl)benzamide (9a) (TG7-181)

$^1$H NMR (CDCl3): δ 7.81 (s, 1H), 7.54 (d, J=7.6 Hz, 1H), 7.50 (d, J=8.8 Hz, 2H), 7.28 (d, J=7.4 Hz, 1H), 7.10 (m, 2H), 6.55 (d, J=9.2 Hz, 2H), 6.0 (t, J=5.4 Hz, 1H), 3.67 (q, J=6.4 Hz, 2H), 3.36 (q, J=6.8 Hz, 2H), 2.99 (t, J=6.4 Hz, 2H), 2.35 (s, 3H), 1.14 (t, J=7.2 Hz, 6H). LCMS (ESI): >97% purity at k 254, MS; m/z, 350 [M+H]+. Anal. Calcd. for C20H23N3O; C, 75.61; H, 7.79; N, 12.02. Found; C, 75.58; H, 7.72; N, 12.07.

TABLE 3

EP2 Bioactivity, DP1 selectivity and aqueous solubility of cinnamic amide analogs

| Entry | Compd. ID | EP2 $K_B$ (nM) | DP1 $K_B$ (nM) | SI (DP1/EP2) | Solubility (μM) |
|---|---|---|---|---|---|
| 15a | TG4-155 | 2.4 | 34.5 | 14.4 | 45 |
| 15b | TG7-23 | 3.4 | 83 | 24 | <25 |
| 15c | TG7-98 | 3.4 | 210 | 60 | <25 |
| 15d | TG6-10-1 | 17.8 | 166 | 9.3 | 27 |
| 15e | TG7-2 | 305 | ND | ND | ND |
| 15f | TG7-13 | 306 | ND | ND | ND |
| 15g | TG7-74 | 2.4 | 110 | 45 | 43 |
| 15h | TG7-76 | 4.9 | 255 | 52 | 41 |
| 15i | TG7-96 | 3.3 | 175 | 53 | <25 |
| 15j | TG7-186 | 11.3 | 900 | 80 | <25 |
| 15k | TG7-122 | 333 | ND | ND | ND |
| 15l | TG7-6 | >1000 | ND | ND | 91 |
| 15m | TG7-9 | >1000 | ND | ND | 180 |
| 15n | TG7-21 | >1000 | ND | ND | 75 |
| 15o | TG7-138 | >1000 | ND | ND | 110 |
| 15p | TG7-109 | >1000 | ND | ND | ND |
| 15q | TG7-91 | >1000 | ND | ND | ND |
| 15r | TG7-95 | 667 | ND | ND | ND |
| 15s | TG7-124 | >1000 | ND | ND | ND |
| 15t | TG7-133 | >1000 | ND | ND | ND |
| 15u | TG7-89 | >1000 | ND | ND | ND |
| 15v | TG4-156 | 214 | ND | ND | ND |
| 15w | TG7-149 | 410 | ND | ND | ND |
| 15x | TG7-128 | 680 | ND | ND | ND |
| 15y | TG7-97 | >1000 | ND | ND | ND |
| 15z | TG7-103 | >1000 | ND | ND | ND |
| 16a | TG8-4 | 11.4 | 505 | 44 | 153 |
| 16b | TG8-16 | 260 | 2820 | 10 | 67 |
| 16c | TG8-21 | 4111 | 7450 | 181 | 235 |
| 16d | TG8-23 | 13.6 | 108 | 7.9 | 68 |
| 16e | TG8-32 | 11.8 | 67.1 | 5.6 | 66 |
| 16f | TG8-27 | 3.7 | 19.9 | 5.3 | 66 |
| 16g | TG8-30 | 58.3 | 198 | 3.4 | 35 |
| 16h | TG7-209 | 340 | ND | ND | ND |
| 16i | TG7-273 | 236 | ND | ND | ND |
| 16j | TG-109-1 | >1000 | ND | ND | ND |

TABLE 3-continued

EP2 Bioactivity, DP1 selectivity and aqueous solubility of cinnamic amide analogs

| Entry | Compd. ID | EP2 $K_B$ (nM) | DP1 $K_B$ (nM) | SI (DP1/EP2) | Solubility (μM) |
|---|---|---|---|---|---|
| 16k | TG8-57 | 84.5 | 752 | 8.9 | ND |
| 16l | TG8-53 | 74.6 | 283 | 3.8 | ND |
| 16m | TG8-56 | 137 | 265 | 2 | ND |
| 16n | TG7-291 | >1000 | ND | ND | ND |
| 16o | TG7-294 | >1000 | ND | ND | ND |
| 16p | TG8-17-1 | >1000 | ND | ND | ND |
| 16q | TG4-94-1 | 16.5 | 66 | 4 | ND |

Schild KB values are calculated using the formula log (dr−1)=log $X_B$-log $K_B$, where dr (dose ratio)=fold shift in $EC_{50}$ of PGE2 by the test compound, $X_B$ is antagonist concentration [1 μM]. $K_B$ value indicates a concentration required to produce a 2-fold rightward shift of PGE2 concentration response curve. The solubility of the compounds is measured in PBS buffer (pH 7.4) with 1% DMSO by nephelometry.

Synthesis and Structure Activity Relationship of 1-Indole Cinnamic Amide Analogs

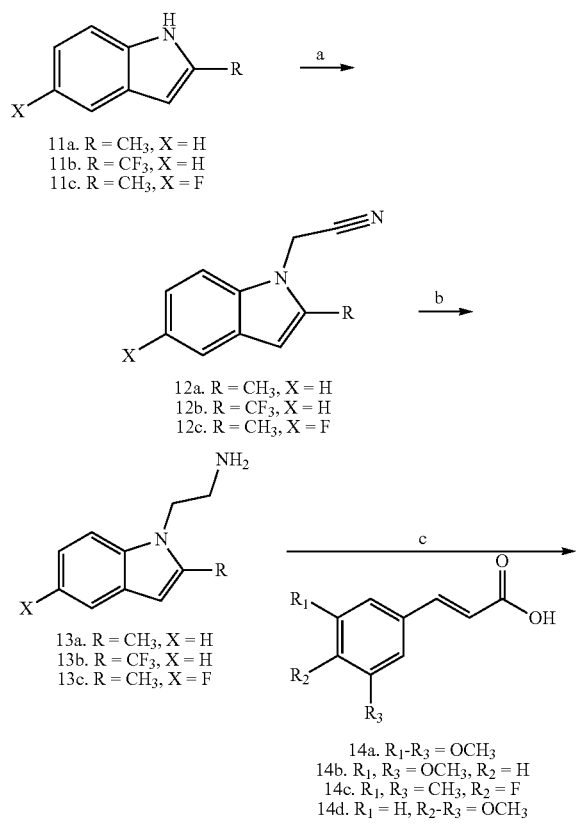

11a. R = $CH_3$, X = H
11b. R = $CF_3$, X = H
11c. R = $CH_3$, X = F

12a. R = $CH_3$, X = H
12b. R = $CF_3$, X = H
12c. R = $CH_3$, X = F

13a. R = $CH_3$, X = H
13b. R = $CF_3$, X = H
13c. R = $CH_3$, X = F

14a. $R_1$-$R_3$ = $OCH_3$
14b. $R_1$, $R_3$ = $OCH_3$, $R_2$ = H
14c. $R_1$, $R_3$ = $CH_3$, $R_2$ = F
14d. $R_1$ = H, $R_2$-$R_3$ = $OCH_3$

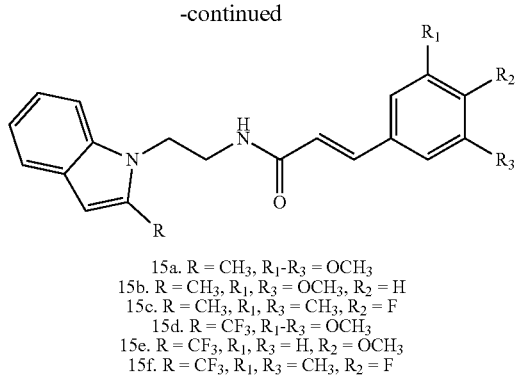

15a. R = $CH_3$, $R_1$-$R_3$ = $OCH_3$
15b. R = $CH_3$, $R_1$, $R_3$ = $OCH_3$, $R_2$ = H
15c. R = $CH_3$, $R_1$, $R_3$ = $CH_3$, $R_2$ = F
15d. R = $CF_3$, $R_1$-$R_3$ = $OCH_3$
15e. R = $CF_3$, $R_1$, $R_3$ = H, $R_2$ = $OCH_3$
15f. R = $CF_3$, $R_1$, $R_3$ = $CH_3$, $R_2$ = F

Indole-2 compounds were prepared as shown wherein step a is NaH, bromoacetonitrile, DMF, 75%; b is Lithium aluminum hydride (LAH), tetrahydrofuran (THF), 32-57%; c is Cinnamic acid derivative (14), 1-ethyl-3-(3-dimethylaminopropyl)-carbodiimide hydrochloride (EDCI), dimethylaminopyridine (DMAP), CH2Cl2, 75-80%. The compound 15a possess sites for structural modification. i) Trimethoxyphenyl group, ii) acryl amide moiety iii) ethylene linker, iv) a methyl group on the indole ring. Compound 15d has a $CF_3$ in place of $CH_3$ on the indole ring. This transformation enhanced metabolic stability (Table 5) and brain and plasma PK properties. The $CF_3$ analog (15d) was about 7-fold less potent for EP2 in comparison to the $CH_3$ analog 15a (Table 4). Several derivatives were prepared that have reduced number of methoxy groups or were completely substituted with other substituents. The synthesis was carried out starting from commercially available 2-methyl indole or 2-trifluoromethyl indoles (11a-c), which on treatment with bromoacetonitrile provided intermediates (12a-c), which then were subjected to lithium aluminum hydride to reduce cyanide to amines. Amines were coupled to 3,4,5-trimethoxycinnamic acid derivatives (14a-c) to provide final products (15a-f). Synthesized derivatives were tested by using a cAMP-derived TR-FRET assay, at single concentration (1 μM) to observe a rightward shift of PGE2 (an EP2 agonist) concentration response curve in a C6G cell line that overexpresses human EP2 receptors. From this a Schild $K_B$ value (a concentration required to cause 2-fold rightward shift of agonist $EC_{50}$) is calculated assuming a Schild slope of 1.07, which is the mean slope determined from four concentration (0.1, 0.3, 1 & 3 μM) Schild plots carried out on several compounds in this series. A similar procedure is carried out with human DP1 receptors at single compound concentration of 10 μM, and used to rank order the analogs based on EP2 potency and selectivity against DP1.

The structure activity relationship (SAR) study indicates a 3,5-dimethoxycinnamic amide derivative (15b) and a compound in which three methoxys are substituted with two methyl groups and a fluorine (15c) display EP2 potency. These derivatives show improved selectivity against DP1 (15b displays 24-fold, and 15c, 60-fold) (Table 3).

Indole-3 Cinnamic Amide Analogs

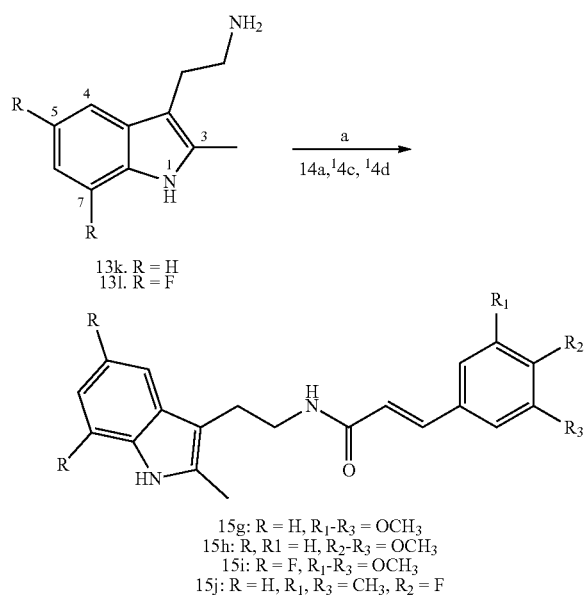

The synthesis of several indole-3-derivatives were explored as shown wherein, step a is cinnamic acid derivative (14a or 14c or 14d), EDCI, DMAP, CH2Cl2. Commercially available 2-(2-methyl-1H-indol-3-yl)ethanamines (13k,l) were coupled to cinnamic acid derivatives (14a, c, d) to synthesize compounds 15g-j. Both indole-positional isomers are active. Incorporation of two fluorine atoms on the indole phenyl ring to block the ortho and para (5th, 7th) positions to the ring nitrogen (15i) maintained EP2 potency compared to 15a. Certain 3-indole derivatives (15g-j) displayed improved selectivity (45 to 80-fold) against DP1 (Table 3).

Figure 4:
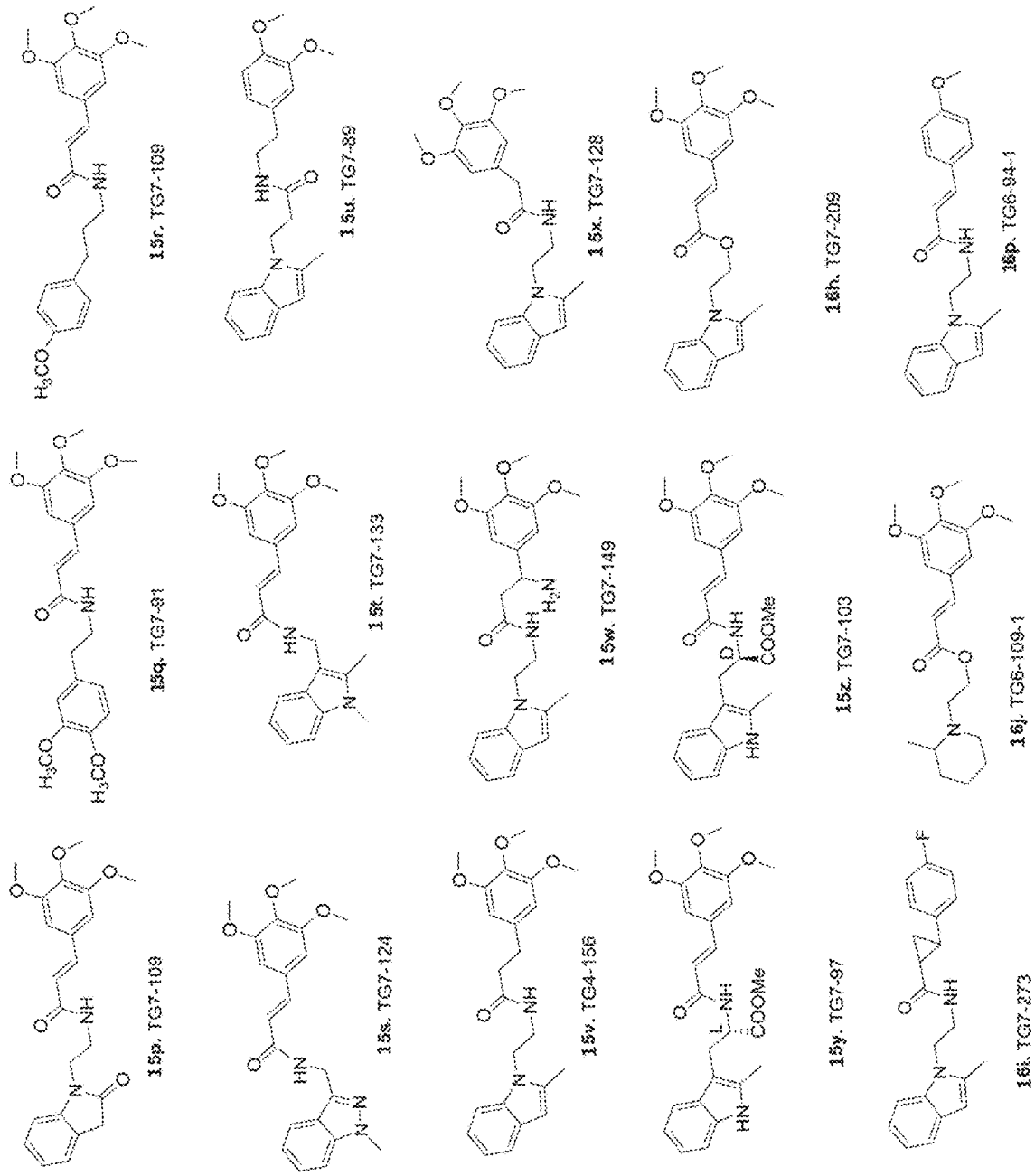
FIG. 4 illustrates certain embodiments of the disclosure.

To determine whether indole ring can be replaced with other structurally equivalent rings, a benzofuran derivative was synthesized starting from 3-bromo-2-methyl furan. This furan showed 138-fold reduced potency compared to its indole equivalents 15a and 15g. Other scaffolds such as indolin-2-one (5p), phenyethyl and phenylpropyl groups (15q, 15r) were examined (FIG. 4). A 2-methylpiperidine ring (in place of indole ring) derivative 16j (FIG. 4) displayed complete loss of activity. Taken together these results suggest that the indole (1- or 3-positional isomers) ring desirable for EP2 potency.

Although several compounds showed high EP2 potency and improved DP selectivity, they displayed minimal aqueous solubility (Table 3). Strategies were explored to improve the aqueous solubility in this class of compounds. First, the indole rings at 2nd and 3rd positions were functionalized with more polar functional groups.

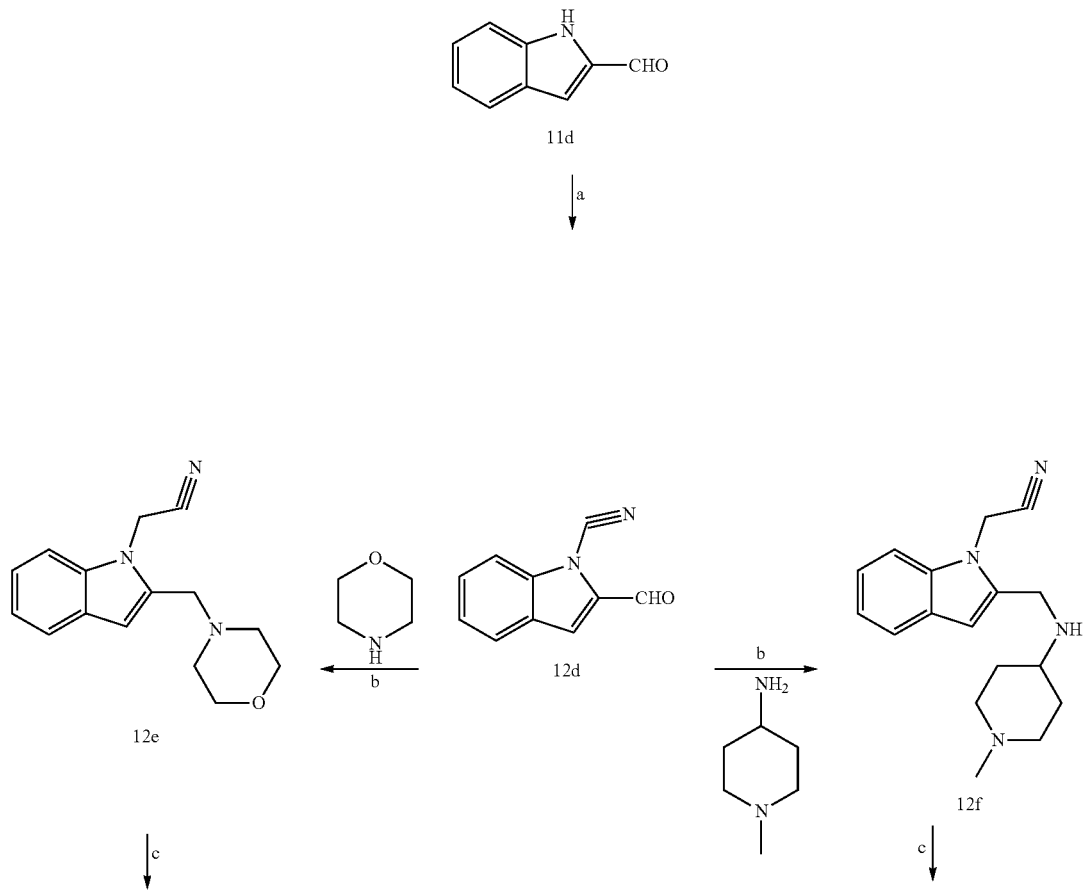

101

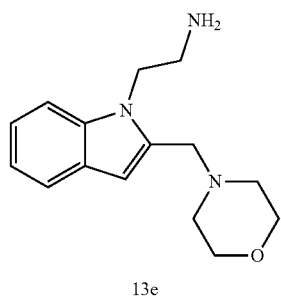

13e

|14a|d
↓

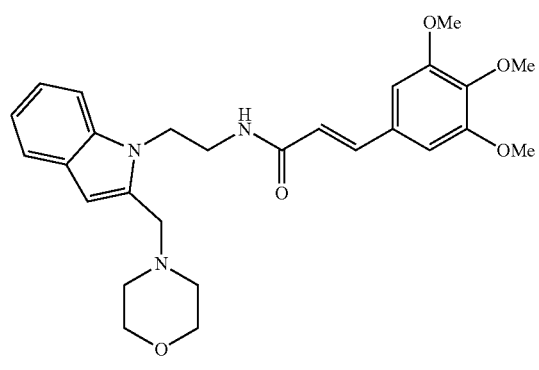

15l

102

-continued

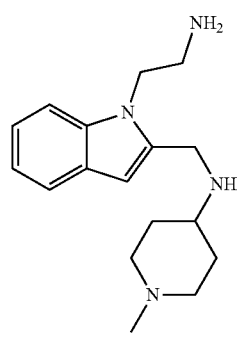

13f

|14a|d
↓

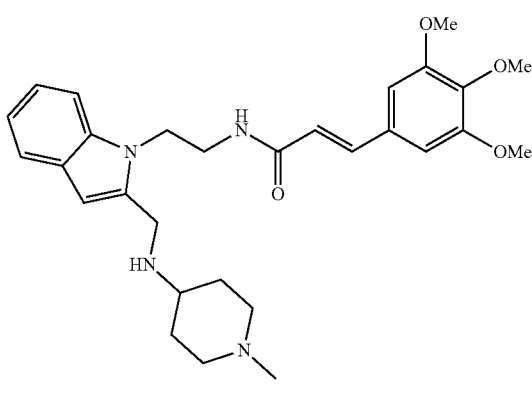

15m

The synthesis is initiated with 2-formyl indole (11d), which on treatment with bromoacetonitrile provided 12d, which then on reductive-amination reaction with morpholine and 4-amino-1-methyl piperidine provided 12e and 12f. These compounds were reduced with lithium aluminum hydride to get 13e and 13f, which were then coupled to 3,4,5- trimethoxycinnamic acid (14a) to provide the products (15l, 15m). Similarly, 3-substituted indoles (15n-o) with more solubilizing functional groups were synthesized. These derivatives (15l-o) and their HCl salts forms have improved solubility in the range of 75-180 μM (Table 3) compared to parents 15a and 15d.

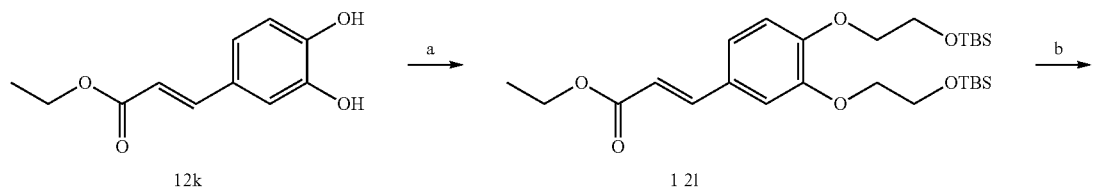

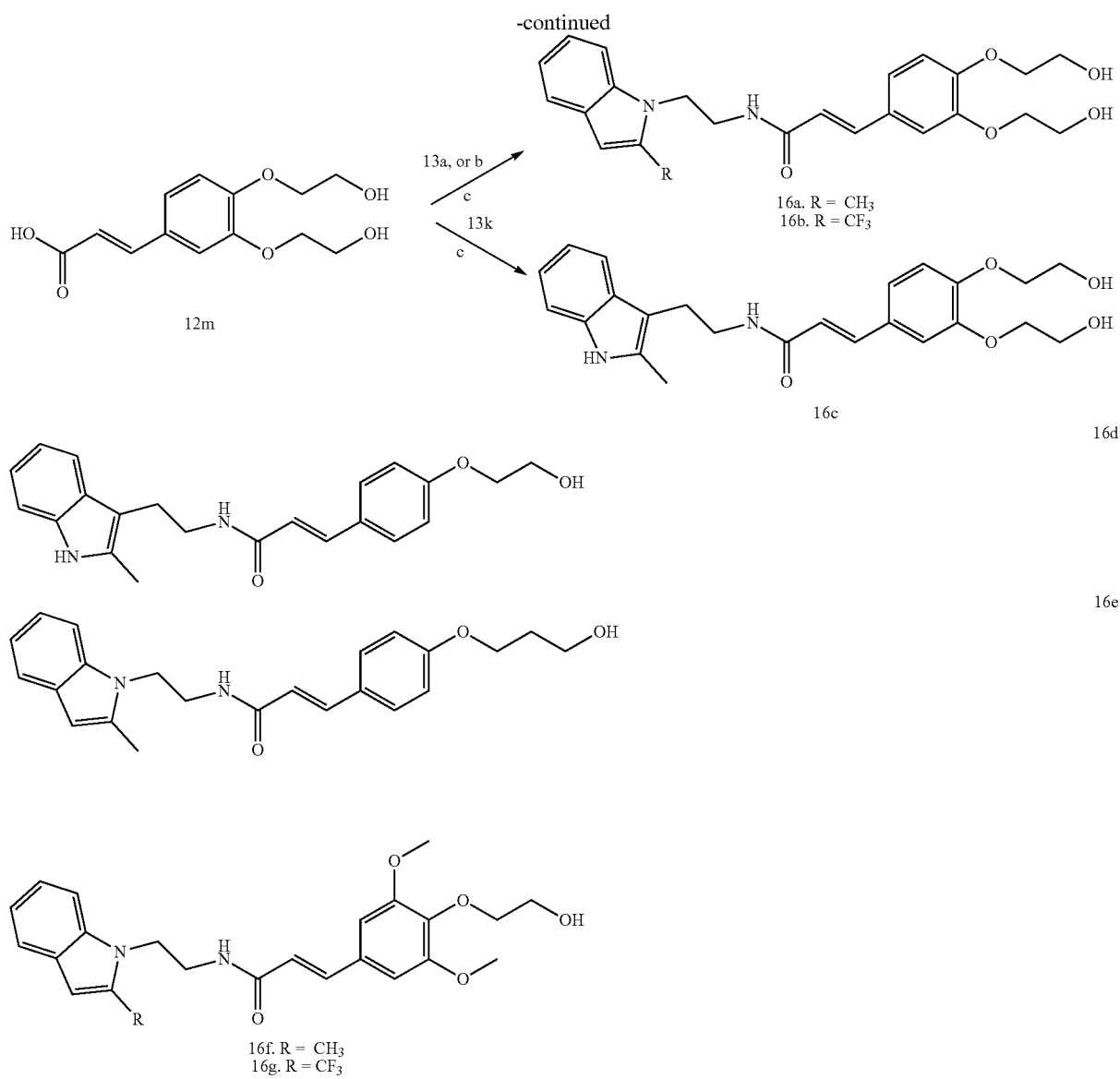

The scaffold 15a and 15d was substituted on the methoxy groups. Commercially available 3,4-dihydroxycinnamic acid ethyl ester (2k) was subjected to Mitsunobu reaction with 2-tertbutyldimethylsilyloxyethanol to get bis-tert-butyldimethylsilyloxyether (12l), which on treatment with 1N NaOH in refluxing tetrahydrofuran, and then quenching with 2N HCl (in one pot) provided precursor acid (12m). This acid was coupled individually to indole amines 13a, 13b or 13k to provide final products (16a-c) with two pendent hydroxyethylether moieties. Compounds 16a, 16c have 3 to 5-fold higher aqueous solubility (Table 3) in comparison to parent compound 5a. A trifluoromethyl indole compound (16b) has shown 2.5-fold higher solubility (67 μM) in comparison to its parent compound 15d (Table 3). Several compounds were synthesized with only one hydroxyethylether or hydroxypropyl ether moieties (16d-16g). These derivatives also showed about 1.2 to 1.4-fold higher solubility than the parents 15a and 15d (Table 3).

Some compounds with improved aqueous solubility have high EP2 potency. For example, compounds 16a, 16d, 16e displayed desirable EP2 potency (Schild KBs 11.4-13.6 nM). These derivatives are less potent than 5a, but are slightly more potent than 15d. Among these three, 16a a bis-hydroxyethylether compound exhibited 44-fold selectivity to DP1 (Table 3). Compound 16c showed very high selectivity (180-fold) to DP1. This compound is very soluble. Moreover, compound 16f, which has two extra methoxy groups in addition to a hydroxyethylether unit, has nearly equal EP2 potency to 15a.

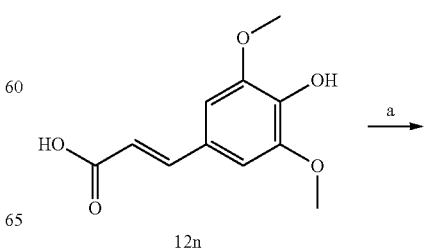

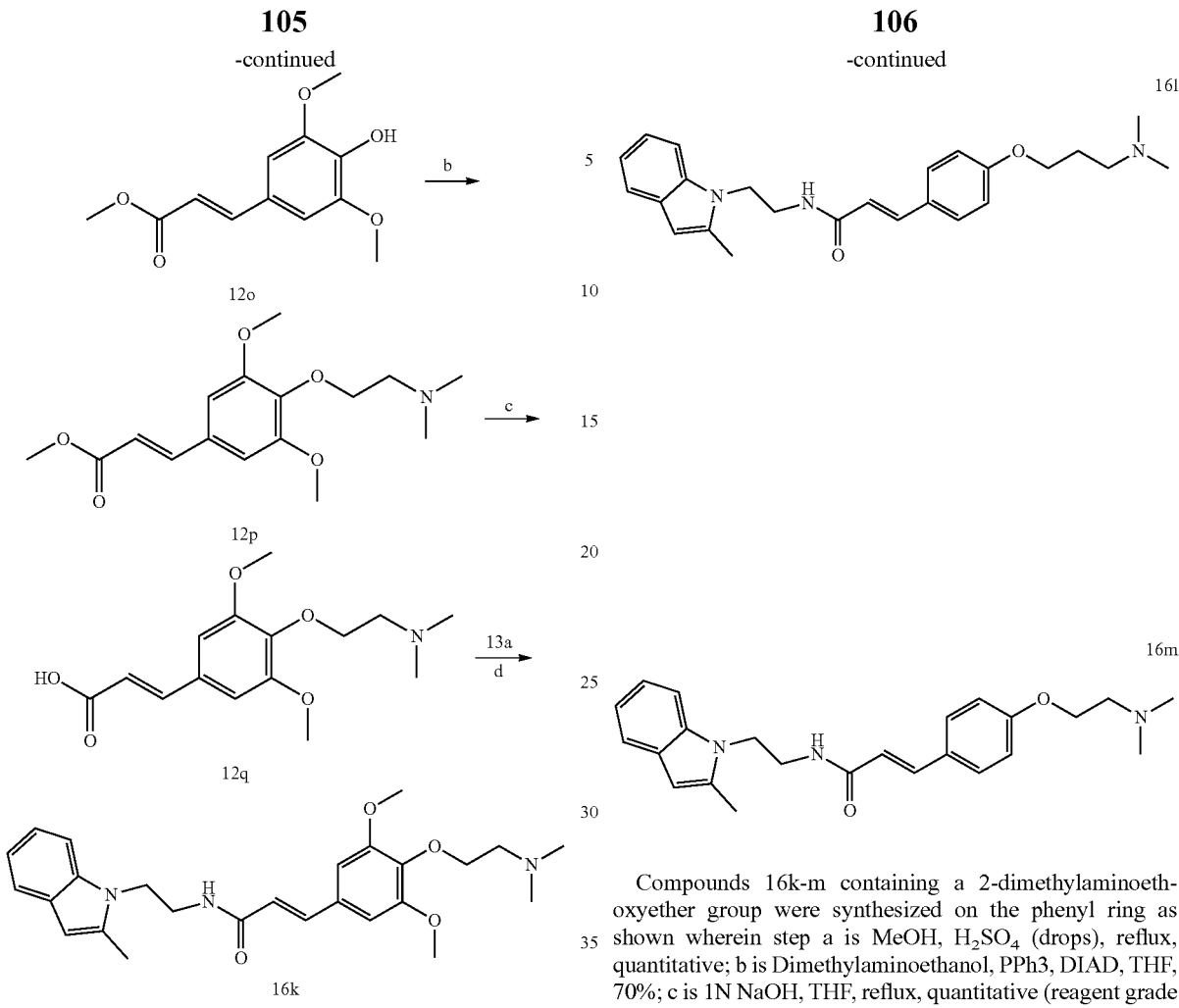
Compounds 16k-m containing a 2-dimethylaminoethoxyether group were synthesized on the phenyl ring as shown wherein step a is MeOH, $H_2SO_4$ (drops), reflux, quantitative; b is Dimethylaminoethanol, PPh3, DIAD, THF, 70%; c is 1N NaOH, THF, reflux, quantitative (reagent grade salt); and d is 13a, EDCI, DMAP, DMF, 70%.
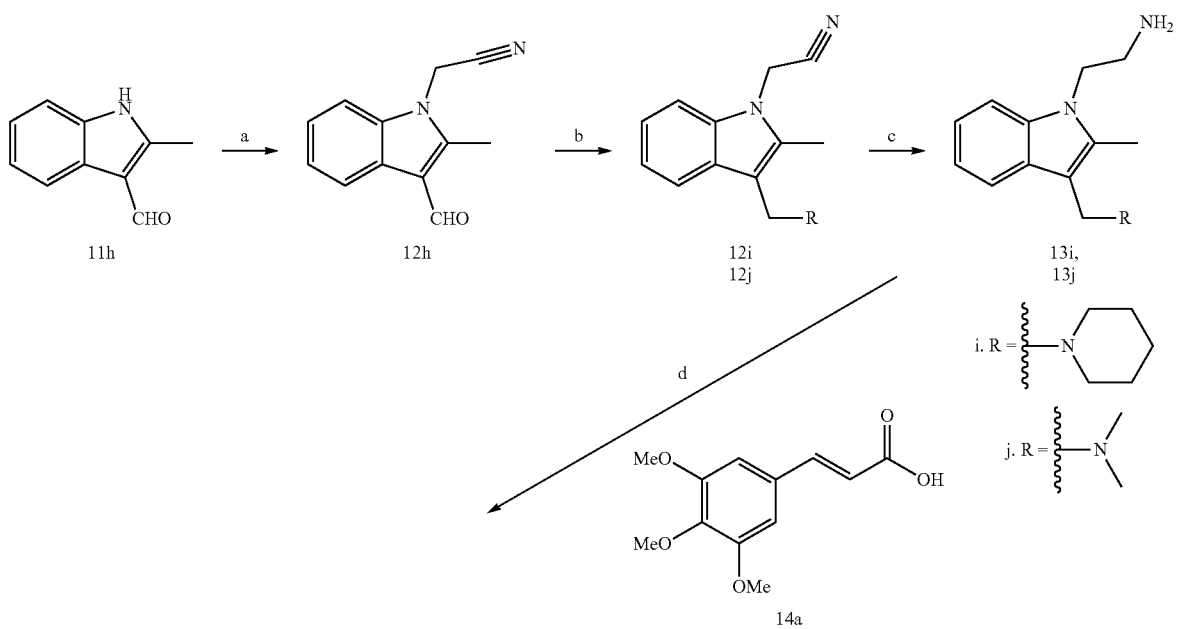

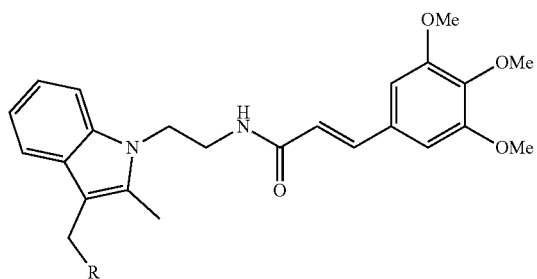

15n. R = piperidine

15o. R = N(CH₃)₂

Compounds were synthesized as shown wherein step a is NaH, bromoacetonitrile, DMF 75%; b is piperidine, or N,Ndimethylamine,Na(OAchBH, AcOH, DCM, 70%; c is LAH, THF, 55% (for 3i), KBH4, Raney-Ni, EtOH, 5% (for 3j); and d is EDCI, DMAP, DCM, 75%.

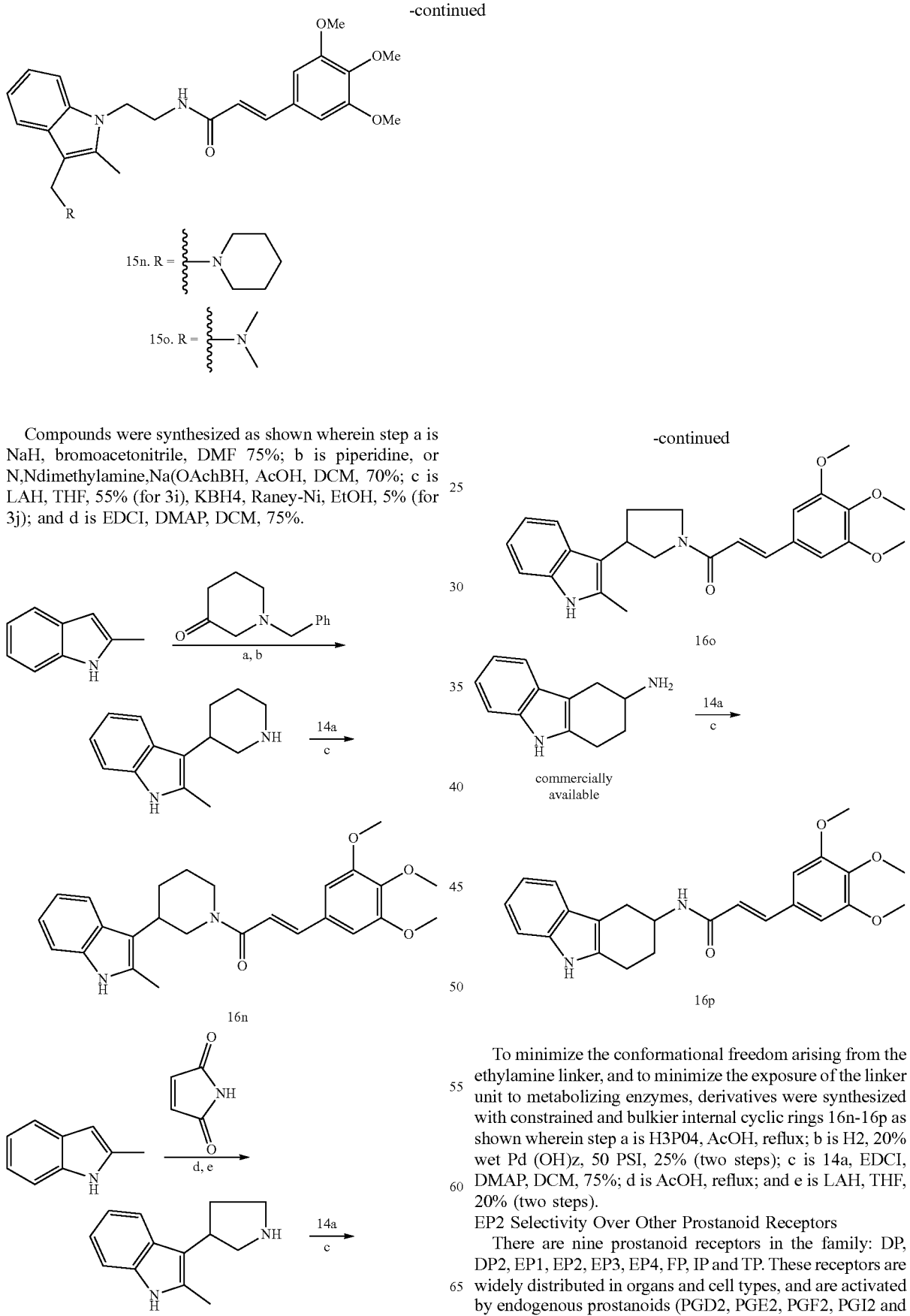

To minimize the conformational freedom arising from the ethylamine linker, and to minimize the exposure of the linker unit to metabolizing enzymes, derivatives were synthesized with constrained and bulkier internal cyclic rings 16n-16p as shown wherein step a is H3P04, AcOH, reflux; b is H2, 20% wet Pd (OH)z, 50 PSI, 25% (two steps); c is 14a, EDCI, DMAP, DCM, 75%; d is AcOH, reflux; and e is LAH, THF, 20% (two steps).

EP2 Selectivity Over Other Prostanoid Receptors

There are nine prostanoid receptors in the family: DP, DP2, EP1, EP2, EP3, EP4, FP, IP and TP. These receptors are widely distributed in organs and cell types, and are activated by endogenous prostanoids (PGD2, PGE2, PGF2, PGI2 and TXA2). Among these receptors, EP1, EP2, EP3 and EP4 share a common endogenous ligand PGE2 for their activation. EP2 and EP4 are positively coupled to cAMP signaling, whereas EP3 inhibits cAMP production and EP1 mediates cytosolic Ca+2 signaling. The DP1 receptor is not activated by PGE2, it has the highest structural homology to EP2, and is known to exert proinflammatory effects similar to EP2 in certain conditions. EP2 receptor also shares a 40% structural homology to the IP receptor. IP receptor activation is shown to play important role in cardioprotection.

Certain synthesized derivatives showed selectivity to DP1 (Table 3). Derivatives 15c, 15g-j, 16a, 16c showed >44-fold selectivity to EP2 over DP. These derivatives were selected for testing against EP4 and IP receptors. Cell lines were created that overexpress EP4 receptors, or IP receptors on C6-glioma cells. A cAMP-derived TR-FRET assay was developed using agonists PGE2 (for EP4) and iloprost (for IP), similar to EP2 assay. The results show that certain analogs display micromolar Schild $K_B$s for EP4 and IP receptors (Table 4), with high selectivity indexes. For example 15c displayed 12,100 fold selectivity against EP4, and over 6,000 fold selectivity against IP receptor.

Compound 15g also displayed high selectivity to EP2 over EP4 (1790-fold) and IP (5310-fold). Likewise compounds 15h and 15j showed 300-, 310-fold selectivity to EP4, 8720-, 1920-fold selectivity to IP receptor (Table 4). Compounds with improved aqueous solubility, for example 16a, displayed 625-fold selectivity against EP4 and 138-fold selectivity against IP; 16c displayed 230-fold selectivity to EP4, and greater than five thousand fold selectivity against IP. Likewise, compounds 16d-f also displayed good selectivity against EP4 and IP receptor (Table 4). Compounds were tested in a cell viability assay against C6 glioma cells (Table 4).

TABLE 4

EP2 potency, selectivity against EP4 and IP receptors, and cytotoxicity of selected EP2 antagonists

| Compd. | $K_B$ EP2 nM | $K_B$ EP4 μM | Selective index (EP4/EP2) | $K_B$ IP μM | Selective Index (IP/EP2) | Cytotoxicity ($CC_{50}$) μM | Therapeutic Index ($CC_{50}$/EP2 $K_B$) |
|---|---|---|---|---|---|---|---|
| 15a (TG4-155) | 2.4 | 11.4 | 4,750 | 62 | 25,800 | 172 | 71,700 |
| 15c (TG7-98) | 3.4 | 41.0 | 12,100 | 22.5 | 6,630 | 368 | 108,200 |
| 15d (TG6-10-1) | 17.8 | 11.2 | 630 | 8.45 | 475 | 81 | 4,550 |
| 15g (TG7-74) | 2.4 | 4.3 | 1,790 | 12.7 | 5,310 | 59.5 | 24,800 |
| 15h (TG7-76) | 4.9 | 1.46 | 300 | 42.7 | 8,720 | 246 | 50,200 |
| 15j (TG7-186) | 11.3 | 3.5 | 310 | 21.7 | 1,920 | 317 | 28,000 |
| 16a (TG8-4) | 11.4 | 7.13 | 625 | 1.57 | 138 | 92.3 | 8,100 |
| 16c (TG8-21) | 41.1 | 9.5 | 230 | 240 | 5,840 | 126 | 3,060 |
| 16d (TG8-23) | 13.6 | 7.58 | 560 | 30.0 | 2,200 | 81.7 | 6,000 |
| 16e (TG8-32) | 11.8 | 5.96 | 505 | 210 | 1,780 | 36.6 | 3,100 |
| 16f (TG8-27) | 3.7 | 7.49 | 2,020 | 85.0 | 23,000 | 43.3 | 11,700 |
| 16g (TG8-30) | 58.3 | 7.93 | 136 | 95.9 | 164 | 31.2 | 535 |

TABLE 5

Liver microsomal stability and in vivo pharmacokinetic properties of selected compounds

| | (% of Parent Compound Remaining at 60 min vs. T = 0 min) | | | | Mouse in vivo pharmacokinetics properties | | | | |
|---|---|---|---|---|---|---|---|---|---|
| | Human Liver Microsomes | | Mouse Liver Microsomes | | Route of administration | C-max | AUC-last | $T_{1/2}$ | B/P |
| Compd. | 1 μM | 10 μM | 1 μM | 10 μM | (dose) | (ng/mL) | (hr*ng/mL) | (plasma) | ratio |
| 15a (TG4-155) | 0.1 | 10.6 | 0.2 | 4.8 | IV (3 mg/kg) | 2400 ± 350 | 749 ± 24 | 0.45 h | 0.3 |
| | | | | | IP (3 mg kg) | 738 ± 207 | 457 ± 64 | 0.58 h | |
| 15c (TG7-98) | 20.9 | 24.0 | 18.3 | 13.0 | ND | ND | ND | ND | ND |
| 15d (TG6-10-1) | 2.3 | 39.9 | 2.0 | 23.1 | IP (5 mg/kg) | 115 ± 303 | 453 ± 49 | 1.6 h | 1.8 |
| | | | | | PO (10 mg/kg) | 248 ± 61 | 475 ± 60 | 1.8 h | 1.6 |
| 15g (TG7-74) | 0.8 | 5.8 | 0 | 0.2 | ND | ND | ND | ND | ND |
| 15h (TG7-76) | 12.4 | 18.6 | 0.2 | 0.1 | ND | ND | ND | ND | ND |

TABLE 5-continued

Liver microsomal stability and in vivo pharmacokinetic properties of selected compounds

| | (% of Parent Compound Remaining at 60 min vs. T = 0 min) | | | | Mouse in vivo pharmacokinetics properties | | | | |
|---|---|---|---|---|---|---|---|---|---|
| | Human Liver Microsomes | | Mouse Liver Microsomes | | Route of administration | C-max | AUC-last | $T_{1/2}$ | B/P |
| Compd. | 1 µM | 10 µM | 1 µM | 10 µM | (dose) | (ng/mL) | (hr*ng/mL) | (plasma) | ratio |
| 15j (TG7-186) | 0.4 | 21.4 | 0.1 | 51.7 | ND | ND | ND | ND | ND |
| 16a (TG8-4) | 16.2 | 43.8 | 1.7 | 8.7 | IP (5 mg/kg) | 1510 ± 142 | 1050 ± 58 | 1.49 h | <0.1 |
| | | | | | PO (10 mg/kg) | 128 ± 23 | 197 ± 26 | 1.44 h | <0.1 |
| 16c (TG8-21 | 58.5 | 70.4 | 7.1 | 19.3 | ND | ND | ND | ND | ND |

Competitive Mechanism of Inhibition

Figure 5:
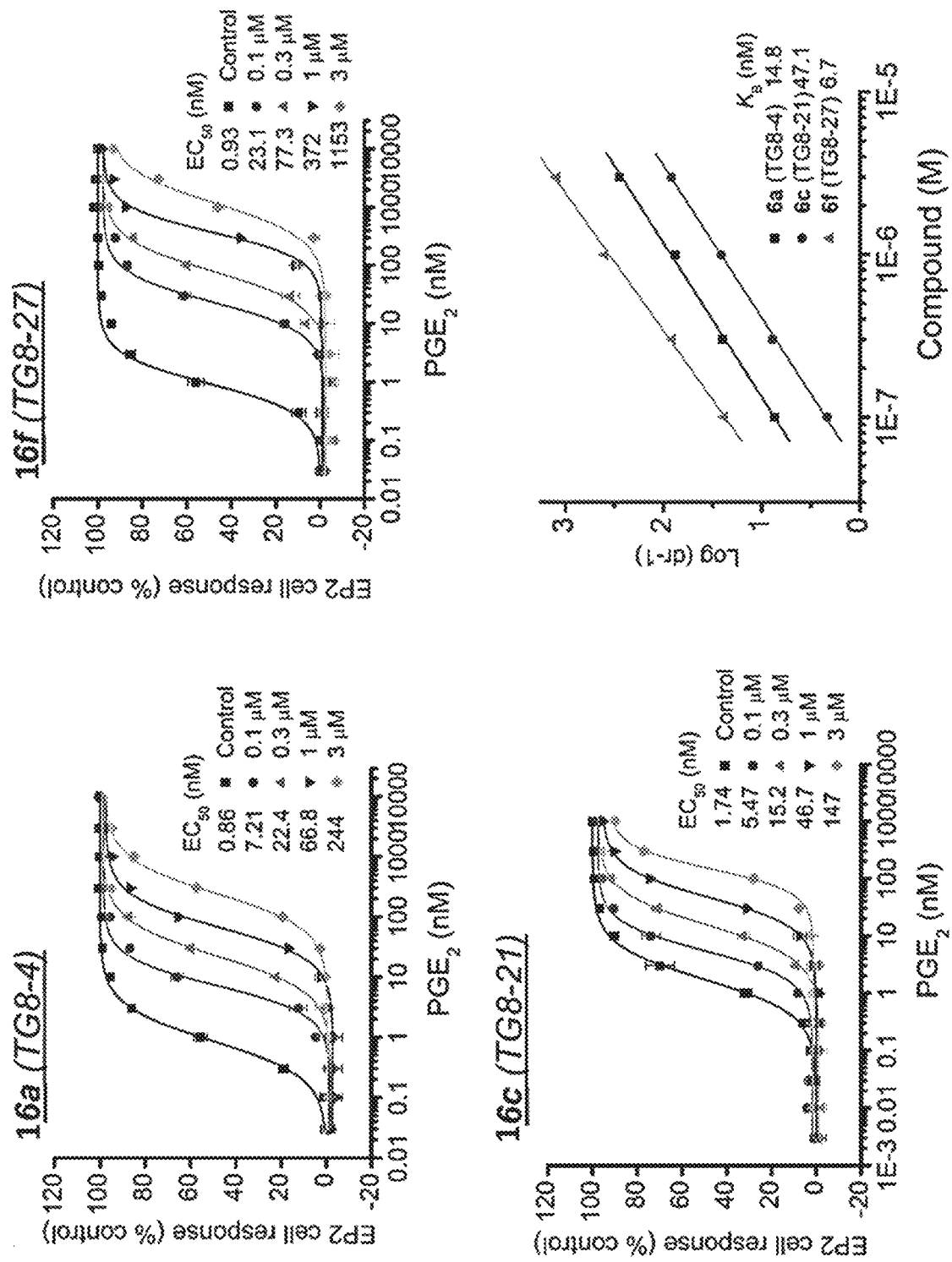
FIG. 5 shows data indicating competitive antagonism of EP2 receptor by acryl amide analogs. Compounds 16a (TG8-4), 16c (TG8-21) and 16f (TG8-27) inhibited $PGE_2$ induced human EP2 receptor activation in a concentration dependent manner. Schild regression analysis is performed to determine the modality of antagonism by these compounds. About 1.1 to 1.8-fold higher $K_B$ values were observed from dose response test in comparison to $K_B$ values derived from a single concentration (1 μM) tests.

Compounds 16a, 16c, and 16f were tested for concentration-response against PGE2 $EC_{50}$ on EP2 receptors. As illustrated in FIG. 5, a linear regression of log (dr−1) on log $X_B$ with slope of unity characterizes a competitive antagonism. Schild $K_B$ values are derived by the equation log (dr−1)=log $X_B$−log $K_B$, where dr=dose ratio, i.e. the fold shift in $EC_{50}$; $X_B$ is [antagonist], and $K_B$ indicates the antagonist concentration required for a twofold rightward shift in the PGE2 concentration-response curve. A lower $K_B$ value indicates a higher inhibitory potency. The compounds induced a concentration-dependent, parallel rightward shift in the PGE2 concentration-response curve (FIG. 5). Schild regression analyses indicate that these compounds have a competitive mechanism of antagonism on EP2 with Schild $K_B$ 14.8 nM for 16a, 47.1 nM for 16c and 6.7 nM for 16f.

EP2 Antagonists Show Improved Microsomal Stability.

Whether compounds show improved metabolic stability in human and mouse liver microsomes was tested. Compound 15a which showed 0.2% remaining at 60 minutes (at 1 µM concentration) in mouse liver microsomes, exhibited an in vivo plasma half-life of about 30 minutes. Compound 15d with 2% remaining at 60 minutes had 1.6 hrs in vivo plasma half-life in mouse (Table 5), suggesting in vitro liver metabolism may be correlated to in vivo plasma half-life in this class. Compound 15c showed high stability in both liver fractions. Interestingly, a 5-fold more aqueous soluble compound 16a showed nearly similar stability in both liver fractions in comparison to 5d. Furthermore, compound 16c which is about 8-fold more soluble than 15d displayed 3-fold improved stability in mouse liver fractions. It is also more stable in human liver microsomal fractions (Table 5), suggesting these two compounds are suitable for in vivo pharmacokinetic study.

Cell-Based cAMP Assay.

Intracellular cAMP was measured with a cell-based homogeneous time-resolved fluorescence resonance energy transfer (TR-FRET) method (Cisbio Bioassays). The assay is based on generation of a strong FRET signal upon the interaction of two molecules, an anti-cAMP antibody coupled to a FRET donor (Cryptate) and cAMP coupled to a FRET acceptor (d2). Endogenous cAMP produced by cells competes with labeled cAMP for binding to the cAMP antibody and thus reduces the FRET signal. Cells stably expressing human DP1, EP2, EP4, or IP receptors were seeded into 384-well plates in 30 µl complete medium (4,000 cells/well) and grown overnight. The medium was carefully withdrawn and 10 µl Hanks' Buffered Salt Solution (HBSS) (Hyclone) containing 20 µM rolipram was added into the wells to block phosphodiesterases. The cells were incubated at room temperature for 0.5-1 h and then treated with vehicle or test compound for 10 min before addition of increasing concentrations of appropriate agonist: BW245C for DP1, PGE2 for EP2 and EP4, or iloprost for IP. The cells were incubated at room temperature for 40 min, then lysed in 10 µl lysis buffer containing the FRET acceptor cAMP-d2 and 1 min later another 10 µl lysis buffer with anti-cAMP-Cryptate was added. After 60-90 min incubation at room temperature, the FRET signal was measured by an Envision 2103 Multilabel Plate Reader (PerkinElmer Life Sciences) with a laser excitation at 337 nm and dual emissions at 665 nm and 590 nm for d2 and Cryptate (50 s delay), respectively. The FRET signal was expressed as: $F665/F590\times10^4$.

General Procedure for Synthesis of 2-(2-substituted-1H-indol-1-yl)acetonitriles (2) from Indoles (1):

A solution of 2-(trifluoromethyl)-1H-indole (11b) (0.5 g, 2.7 mmol) in DMF (2.5 mL) was added to a suspension of NaH (160 mg, 1.5 eq) in DMF (3 mL) at 0° C., and the resulting reaction mixture was stirred for 30 minutes. Then bromoacetonitrile (0.27 mL, 1.5 eq) in DMF (2.5 mL) was introduced into the above reaction at 0° C., and then the reaction was brought to room temperature overnight. Water (20 mL) was added to quench the reaction, then the product was extracted with ethyl ether (30 mL×3). Organics were washed with water, brine and dried over Na2SO4 and concentrated. The crude mass on silica gel chromatography, eluting with 0-10% ethyl acetate furnished (12b) (865 mg, 71% yield; 85% based on recovered starting material).

2-(2-Trifluoromethyl-1H-indol-1-yl)acetonitrile (12b). $^1$H NMR (CDCl$_3$): δ 7.70 (d, J=8 Hz, 1H), 7.44 (m, 2H), 7.28 (txd, J=7.2, 1.6 Hz, 1H), 7.04 (s, 1H), 5.1 (s, 2H). LCMS (ESI): >95% purity at λ 254, MS; m/z, 225 [M+H]+.

General Procedure for Synthesis 2-(2-substituted-1H-indol-1-yl)ethanamines (3) from Acetonitriles (12).

A solution of 12b (855 mg, 3.81 mmol) in THF (30 mL) was added LAH (1M, 9.54 mmol, 2.5 eq), dropwise at 0° C., and the resulting reaction mixture was brought to room temperature overnight. Methanol (2 mL) was slowly added to quench the reaction at −78° C., followed by 1N NaOH (3 mL) at room temperature. The product was extracted with ethyl ether (30 ml×3). Organics were washed with water, brine and dried over Na2SO4 and concentrated. The crude mass was subjected to silica gel chromatography, eluting with 0-5% methanol in dichloromethane to provide 13b (490 mg, 56% yield).

2-(2-(Trifluoromethyl)-1H-indol-1-yl)ethanamine (13b). $^1$H NMR (CDCl3): δ 7.66 (d, J=8 Hz, 1H), 7.44 (dd, J=8.4, 0.8 Hz, 1H), 7.34 (txd, J=7.6, 0.8 Hz, 1H), 7.17 (txd, J=7.4, 1.2 Hz, 1H) 6.94 (s, 1H), 4.28 (t, J=6.8 Hz, 2H) 3.12 (t, J=6.8 Hz, 2H) 2.45 (s, 3H). LCMS (ESI): >97% purity at k 254, MS; m/z, 229 [M+H]+.

General Procedures for Synthesis of Cinnamic Amide Final Products:

A solution of 13b (480 mg, 2.1 mmol) in dichloromethane (10 mL), was added (E)-3-(3,4,5-trimethoxyphenyl)acrylic acid (14a) (504 mg, 1 eq), 1-ethyl-3-(3-dimethylaminopropyl)-carbodiimide hydrochloride (EDCI) (523 mg, 1.3 eq), and N,N-dimethylaminopyridine (10 mg) and resulting reaction mixture was stirred at room temperature for 8 hrs. The reaction was quenched with water (10 mL), and the product was extracted with ethyl acetate (20 mL×3).

Organics were washed with 1% HCl (10 mL), saturated NaHCO3 (10 mL), water (20 mL), brine solution (20 mL), and dried over Na2SO4. The crude product was purified by silica gel chromatography eluting with 0-35% ethyl acetate in hexane to provide 15d. (700 mg, 74% yield).

(E)-N-(2-(2-(Trifluoromethyl)-1H-indol-1-yl)ethyl)-3-(3,4,5-trimethoxyphenyl)acrylamide (15d) $^1$H NMR (CDCl$_3$): δ 7.59 (d, J=8 Hz, 1H), 7.54 (d, J=8.4, Hz, 1H), 7.50 (d, J=15.2 Hz, 1H), 7.27 (q, J=7.2 Hz, 1H), 7.1 (t, J=7.2 Hz, 1H), 6.89 (s, 1H), 6.63 (s, 2H), 6.4 (t, J=6 Hz, 1H), 6.25 (d, J=15.2 Hz, 1H), 4.4 (t, J=6.4 Hz, 1H), 3.8 (s, 3H), 3.76 (s, 6H), 3.69 (q, J=6.4 Hz, 2H). LCMS (ESI): >95% purity at λ 254, MS; m/z, 449 [M+H]+. Anal. Cald. for C23H23F3N2O4: C, 61.60; H, 5.17; N, 6.25. Found: C, 61.34; H, 5.10; N, 6.16.

General Synthesis for 2-Hydroxyethyl- or 2-Dimethylaminoethyl Cinnamic Acids

Step-1: To a solution of ethyl-3,4-dihydroxycinnamate (12k) (460 mg, 2.21 mmol), 2-tert-butyldimethylsilyloxyethanol (2 ml, 9.52 mmol 4.3 eq), triphenylphosphine (3.43 g, 13 mmol, 5.8 mmol) in THF (40 mL), diisopropyl azodicarboxylate (2.4 mL, 12 mmol, 5.3 eq) was added dropwise at 0° C., then the resulting solution was refluxed for 36 hrs. The volatiles were removed under vacuum and the crude product was subjected to silica gel chromatography eluting with 0-20% ethyl acetate in hexane to furnish 12l (775 mg, 67%).

Ethyl (E)-3-(3,4-bis(2-((tert-butyldimethylsilyl)oxy)ethoxy)phenyl)acrylate (12l). $^1$H NMR (CDCl3): δ 7.60 (d, J=15.6 Hz, 1H), 7.07 (dd, J=6.8, 1.6 Hz, 1H), 7.04 (d, J=2 Hz, 1H), 6.87 (d, J=8.4 Hz, 1H), 6.26 (d, J=16 Hz, 1H) 4.24 (q, J=6.8 Hz, 2H), 4.07 (q, J=5.6 Hz, 4H), 3.97 (t, J=5.6 Hz, 4H), 1.30 (t, J=7.2 Hz, 3H), 0.88 (two singlets, 18H), 0.08 (two singlets, 12H). LCMS (ESI): >95% purity at k 254, MS; m/z, 525 [M+H]+.

Step-2: A solution of 12l (375 mg, 0.71 mmol) in THF (10 mL) was added 1N NaOH (2.13 mL, 2.13 mmol, 3 eq) and the resulting reaction was refluxed for 48 hrs. The reaction mixture was cooled and neutralized with 1N HCl (10 mL) to pH 4. Then the product was extracted with ethyl acetate (25 mL×3). Organics were dried over Na2SO4 and concentrated to dryness under vacuum to furnish 12m (190 mg, quantitative yield), which was used for next step without further purification. (E)-3-(3,4-bis(2-hydroxyethoxy)phenyl)acrylic acid (12m). $^1$H NMR (DMSO-d6): δ 12.0 (bs, 1H), 7.46 (d, J=15.6 Hz, 1H), 7.29 (d, J=2 Hz, 1H), 7.14 (m, 1H), 6.96 (d, J=8 Hz, 1H), 6.38 (d, J=16 Hz, 1H) 4.0 (m, 4H), 3.68 (bs, 4H). LCMS (ESI): >95% purity at k 254, MS; m/z, 267 [M−H].

(E)-3-(3,4-bis(2-hydroxyethoxy)phenyl)-N-(2-(2-methyl-1H-indol-1-yl)ethyl)acrylamide (16a, TG8-4). This compound was prepared from 12m and 13a in 80% yield, by the method described for 15d. $^1$H NMR (CDCl$_3$): δ 7.46 (d, J=8.8 Hz, 1H), 7.43 (d, J=16 Hz, 1H), 7.26 (d, J=9.6 Hz, 1H), 7.07 (t, J=6.8 Hz, 1H), 7.04 (t×d, J=8.4, 2 Hz, 2H), 6.81 (d, J=8 Hz, 1H), 6.12 (d, J=15.6 Hz, 1H), 4.25 (t, J=6 Hz, 2H), 4.04 (q, J=4 Hz, 4H), 3.87 (q, J=4.4 Hz, 4H), 3.62 (t, J=5.6 Hz, 2H), 2.34 (s, 3H). LCMS (ESI): >97% purity at k 254, MS; m/z, 425 [M+H]+. HRFABMS: Calcd. for C24H28N2O5Na, 447.18904; found 447.18976.

(E)-3-(3,4-bis(2-hydroxyethoxy)phenyl)-N-(2-(2-methyl-1H-indol-3-yl)ethyl)acrylamide (16c, TG8-21). This compound was prepared from 12m and 13k in 80% yield, by the method described for 15d. $^1$H NMR (CDCl3+MeOH-d4): δ 7.41 (d, J=7.2 Hz, 1H), 7.34 (d, J=15.6 Hz, 1H), 7.19 (d×t, J=8.4, 0.8 Hz, 1H), 6.92 (m, 4H), 6.77 (d, J=8 Hz, 1H), 6.10 (d, J=16 Hz, 1H), 3.99 (t, J=4 Hz, 4H), 3.81 (q, J=3.6 Hz, 4H), 3.48 (t, J=6.8 Hz, 2H), 2.87 (t, J=7.2 Hz, 2H), 2.27 (s, 3H). LCMS (ESI): >97% purity at k 254, MS; m/z, 425 [M+H]+. HRFABMS: Calcd. For C24H28N2O5Na, 447.18904; found 447.18889.

General Procedure for Synthesis Isoxazole and Pyrazole

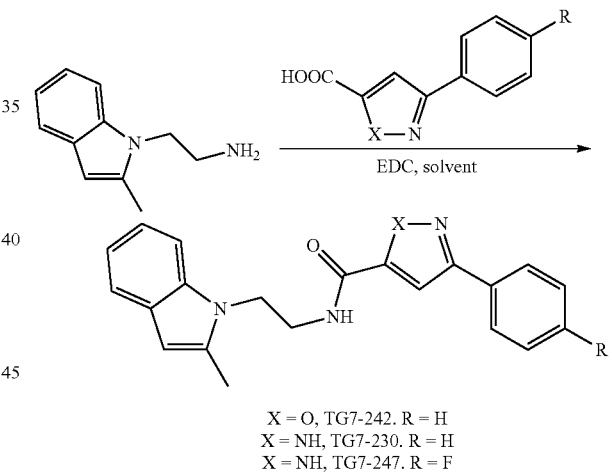

X = O, TG7-242. R = H
X = NH, TG7-230. R = H
X = NH, TG7-247. R = F

The synthesis of TG7-230 and TG7-242 was analogous to several other compounds where amine precursor was coupled to either an oxazole or pyrazole carboxylic acid in the presence of catalyst EDCI or co-catalysts, for example DMAP and in a solvent dichloromethane or dimethylformamide or mixture to provide the product upon silica gel chromatography or recrystallisation with methanol.

TG7-230. δ 7.6 (d, J=7.2 Hz, 2H), 7.45 (d, J=7.6 Hz, 1H), 7.37 (t, J=7.2 Hz, 2H), 7.30 (t, J=7.2 Hz, 2H), 7.07 (t, J=8 Hz, 1H), 7.0 (t, J=8 Hz, 1H), 6.18 (s, 11), 4.27 (t, J=6.4 Hz, 2H), 3.67 (t, J=6.4 Hz, 2H), 2.35 (s, 3H). LCMS (ESI): >97% purity at λ 254, MS; m/z, 345 (M+H).

TG7-242. δ 7.80 (m, 2H), 7.52 (d, J=7 Hz, 1H), 7.48 (m, 3H), 7.31 (d, J=7 Hz, 1H), 7.22 (s, 2H), 7.15 (t, J=8 Hz, 1H), 7.07 (t, J=8 Hz, 1H), 6.66 (bs, 1H), 6.28 (s, 1H), 4.38 (t, J=6 Hz, 2H), 3.80 (t, J=6 Hz, 2H), 2.40 (s, 3H). LCMS (ESI): >97% purity at λ 254, MS; m/z, 346 (M+H).

TABLE 6
EP2 receptor antagonists: Bioactivity and selectivity against DP1 receptor. ND = not determined
| Compound | Structure | Mol. Wt. | EP2 K$_B$ (nM) | DP1 K$_B$ (nM) |
|---|---|---|---|---|
| TG7-112-2 | 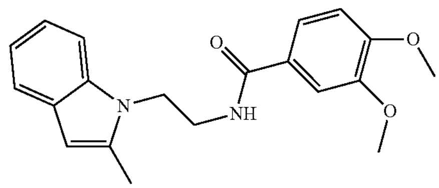 [SMILES: COc1ccc(C(=O)NCCn2c(C)cc3ccccc32)cc1OC] | 338 | 26.7 | 1,350 |
| TG7-242 | 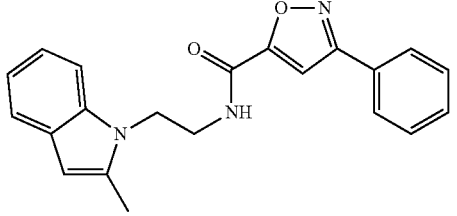 [SMILES: Cc1cc2ccccc2n1CCNC(=O)c1cc(-c2ccccc2)no1] | 345 | 29.5 | Inactive |
| TG7-245 | 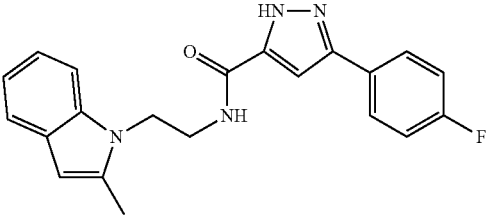 [SMILES: Cc1cc2ccccc2n1CCNC(=O)c1cc(-c2ccc(F)cc2)n[nH]1] | 362 | 22.7 | 140,000 |
| TG7-266 | 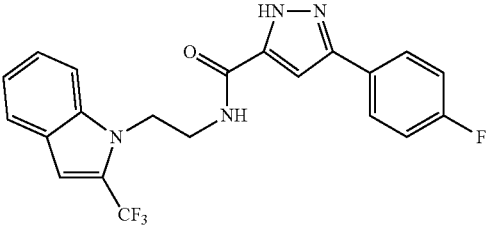 [SMILES: O=C(NCCn1c(C(F)(F)F)cc2ccccc21)c1cc(-c2ccc(F)cc2)n[nH]1] | 416 | 8,798 | ND |
| TG7-274 | 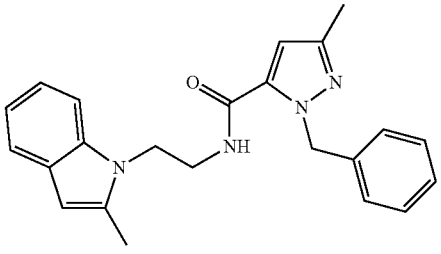 [SMILES: Cc1cc(C(=O)NCCn2c(C)cc3ccccc32)n(Cc2ccccc2)n1] | 372 | 1,329 | ND |
| TG7-275 | 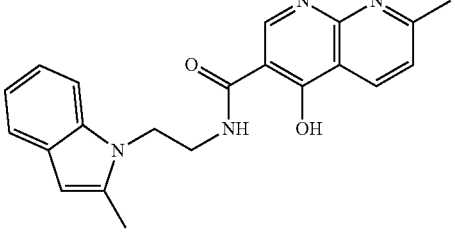 | 360 | 1812 | ND |

TABLE 6-continued
EP2 receptor antagonists: Bioactivity and selectivity against DP1 receptor. ND = not determined
| Compound | Structure | Mol. Wt. | EP2 K$_B$ (nM) | DP1 K$_B$ (nM) |
|---|---|---|---|---|
| TG7-276 | 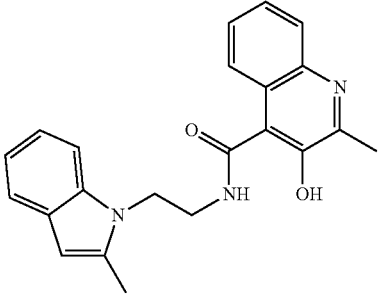 [SMILES: Cc1nc2ccccc2c(C(=O)NCCn2c(C)cc3ccccc32)c1O] | 359 | Inactive | ND |
| TG7-277 | 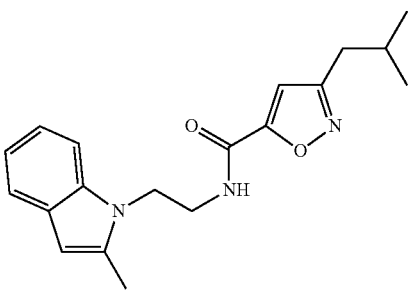 [SMILES: Cc1cc2ccccc2n1CCNC(=O)c1cc(CC(C)C)no1] | 325 | 172 | ND |
| TG7-292 | 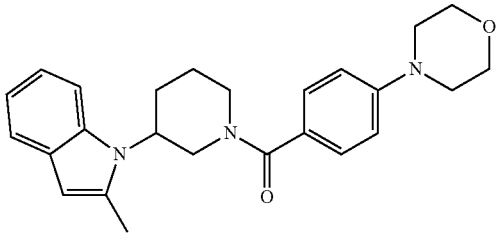 [SMILES: Cc1cc2ccccc2n1C1CCCN(C(=O)c2ccc(N3CCOCC3)cc2)C1] | 403 | 1,790 | Inactive |
| TG7-297 | 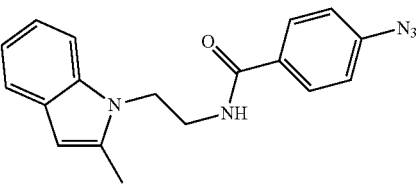 [SMILES: Cc1cc2ccccc2n1CCNC(=O)c1ccc(N=[N+]=[N-])cc1] | 319 | 89.4 | 1889 |
| TG7-300 | 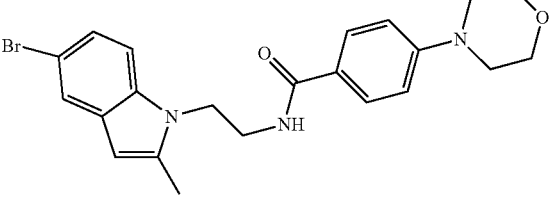 | 411 | 247 | 18930 |
| TG8-3 | 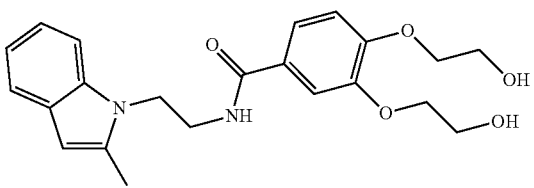 [SMILES: Cc1cc2ccccc2n1CCNC(=O)c1ccc(OCCO)c(OCCO)c1] | 398 | 271 | 62,857 |

TABLE 6-continued

EP2 receptor antagonists: Bioactivity and selectivity against DP1 receptor. ND = not determined

| Compound | Structure | Mol. Wt. | EP2 K$_B$ (nM) | DP1 K$_B$ (nM) |
|---|---|---|---|---|
| TG8-12 | 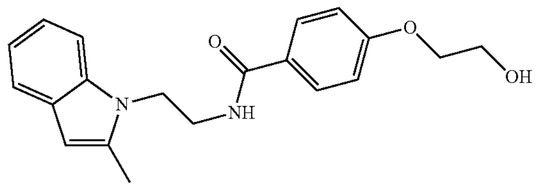 [SMILES: Cc1cc2ccccc2n1CCNC(=O)c1ccc(OCCO)cc1] | 338 | 133 | 2,736 |
| TG8-42 | 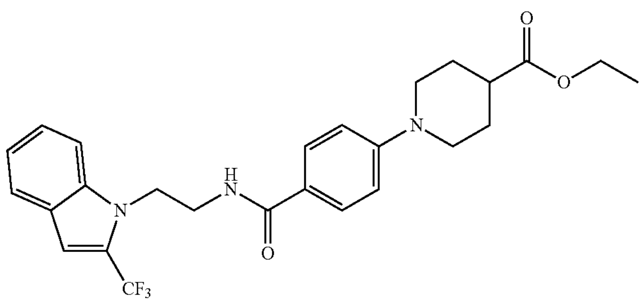 [SMILES: CCOC(=O)C1CCN(c2ccc(C(=O)NCCn3c(C(F)(F)F)cc4ccccc43)cc2)CC1] | 487 | 2,741 | 3,235 |
| TG8-47 | 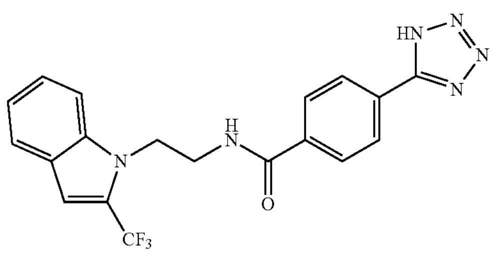 [SMILES: O=C(NCCn1c(C(F)(F)F)cc2ccccc21)c1ccc(-c2nnn[nH]2)cc1] | 400 | 1,112 | 795 |
| TG8-46 | 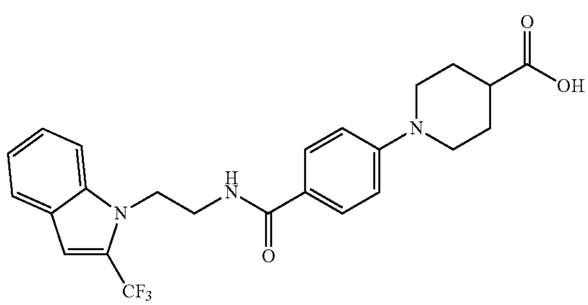 [SMILES: O=C(NCCn1c(C(F)(F)F)cc2ccccc21)c1ccc(N2CCC(C(=O)O)CC2)cc1] | 459 | 413 | 1,060 |
| TG8-52 | 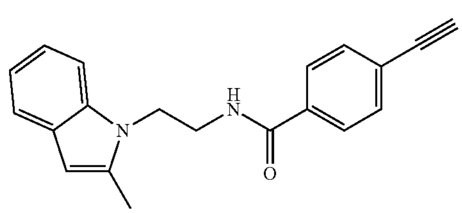 [SMILES: C#Cc1ccc(C(=O)NCCn2c(C)cc3ccccc32)cc1] | 302 | 77.5 | 609 |
| TG8-54 | 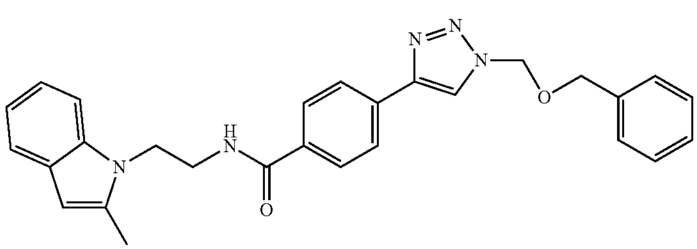 [SMILES: Cc1cc2ccccc2n1CCNC(=O)c1ccc(-c2cn(COCc3ccccc3)nn2)cc1] | 465 | 164 | 3,395 |

TABLE 6-continued

EP2 receptor antagonists: Bioactivity and selectivity against DP1 receptor. ND = not determined

| Compound | Structure | Mol. Wt. | EP2 $K_B$ (nM) | DP1 $K_B$ (nM) |
|---|---|---|---|---|
| TG8-55 | 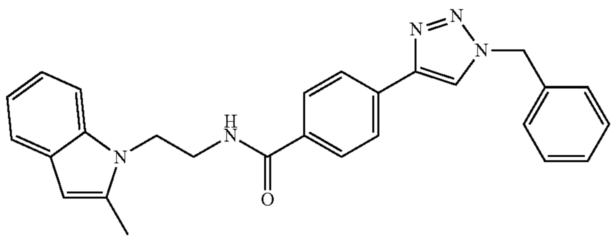 [SMILES: Cc1cc2ccccc2n1CCNC(=O)c1ccc(-c2cn(Cc3ccccc3)nn2)cc1] | 435 | 305 | 6,962 |
| TG8-59 | 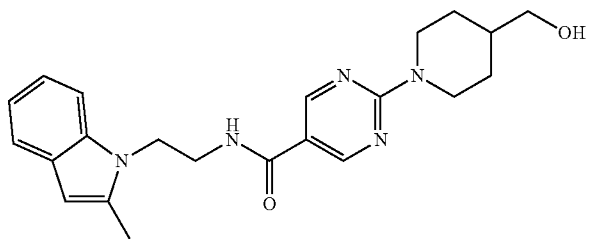 [SMILES: Cc1cc2ccccc2n1CCNC(=O)c1cnc(N2CCC(CO)CC2)nc1] | 393 | 159 | 5,851 |
| TG8-60 | 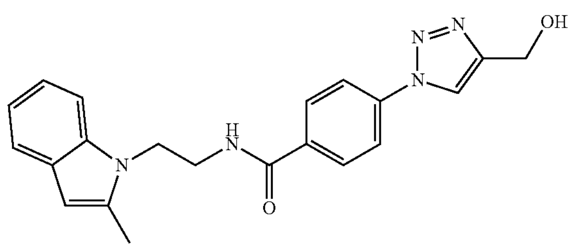 [SMILES: Cc1cc2ccccc2n1CCNC(=O)c1ccc(-n2cc(CO)nn2)cc1] | 375 | 28.2 | 2,423 |
| TG8-64 | 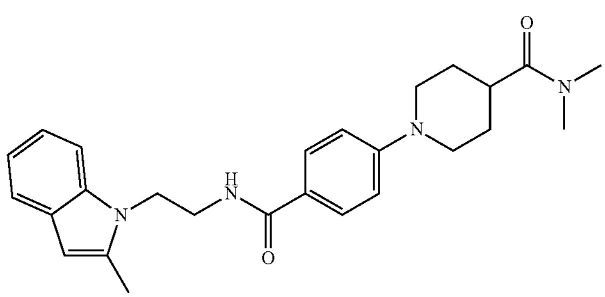 [SMILES: Cc1cc2ccccc2n1CCNC(=O)c1ccc(N2CCC(C(=O)N(C)C)CC2)cc1] | 432 | 190 | ND |
| TG8-69 | 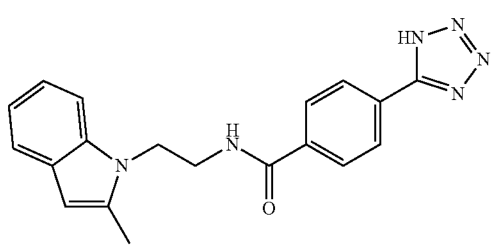 [SMILES: Cc1cc2ccccc2n1CCNC(=O)c1ccc(-c2nnn[nH]2)cc1] | 346 | 26 | ND |
| TG8-75 | 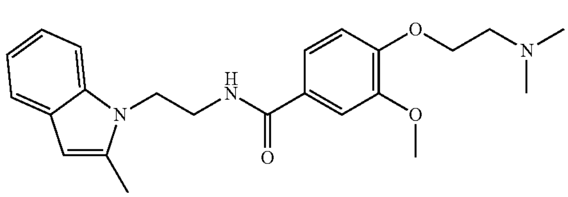 [SMILES: COc1cc(C(=O)NCCn2c(C)cc3ccccc32)ccc1OCCN(C)C] | 395 | 1,000 | ND |

TABLE 6-continued

EP2 receptor antagonists: Bioactivity and selectivity against DP1 receptor. ND = not determined

| Compound | Structure | Mol. Wt. | EP2 $K_B$ (nM) | DP1 $K_B$ (nM) |
|---|---|---|---|---|
| TG8-76-2 | 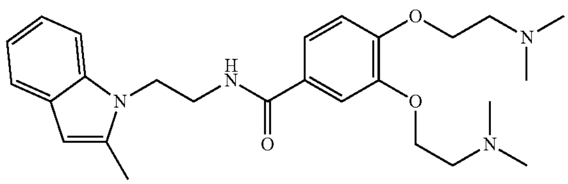 [SMILES: Cc1cc2ccccc2n1CCNC(=O)c1ccc(OCCN(C)C)c(OCCN(C)C)c1] | 452 | Inactive | ND |

The invention claimed is:

1. A method of treating endometriosis comprising administering an effective amount of N-(2-(2-methyl-1H-indol-3-yl)ethyl)-4-(1H-tetrazol-5-yl)benzamide or salt thereof to a subject in need thereof.

2. A method of treating arthritis comprising administering an effective amount of N-(2-(2-methyl-1H-indol-3-yl)ethyl)-4-(1H-tetrazol-5-yl)benzamide or salt thereof to a subject in need thereof.

3. The method of claim 2, wherein the arthritis is rheumatoid arthritis, enthesitis-related arthritis, or psoriatic arthritis.

4. A method of treating cancer comprising administering an effective amount of N-(2-(2-methyl-1H-indol-3-yl)ethyl)-4-(1H-tetrazol-5-yl)benzamide or salt thereof to a subject in need thereof.

5. The method of claim 4 wherein the cancer is skin, blood vessel, lung, head, neck, prostate, colon, ovary, or breast cancer.

6. The method of claim 4 wherein the cancer is hepatocellular carcinoma.

* * * * *